US012788314B2

(12) United States Patent
Kunickas

(10) Patent No.: US 12,788,314 B2
(45) Date of Patent: Nov. 10, 2026

(54) SLEEP CYCLE-BASED WEARABLE VIBRATION ALARM SYSTEM AND METHOD

(71) Applicant: Tadas Kunickas, Brookfield, IL (US)

(72) Inventor: Tadas Kunickas, Brookfield, IL (US)

(73) Assignee: TAVO SLEEP, LLC, Brookfiled, IL (US)

( * ) Notice: Subject to any disclaimer, the term of this patent is extended or adjusted under 35 U.S.C. 154(b) by 181 days.

(21) Appl. No.: 18/759,465

(22) Filed: Jun. 28, 2024

(65) Prior Publication Data

US 2025/0000451 A1 Jan. 2, 2025

Related U.S. Application Data

(60) Provisional application No. 63/523,818, filed on Jun. 28, 2023.

(51) Int. Cl.

| | |
|---|---|
| ***B60K 28/06*** | (2006.01) |
| ***A61B 5/00*** | (2006.01) |
| ***A61B 5/11*** | (2006.01) |
| ***B60W 60/00*** | (2020.01) |
| ***G08B 6/00*** | (2006.01) |
| ***H04M 1/72409*** | (2021.01) |
| ***H04M 1/72451*** | (2021.01) |

(52) U.S. Cl.
CPC .............. *A61B 5/4812* (2013.01); *A61B 5/11* (2013.01); *A61B 5/6831* (2013.01); *A61B 5/7264* (2013.01); *A61B 5/743* (2013.01); *A61B 5/7435* (2013.01); *A61B 5/7455* (2013.01); *G08B 6/00* (2013.01); *H04M 1/72409* (2021.01); *H04M 1/72451* (2021.01); *A61B 2560/0214* (2013.01); *A61B 2560/045* (2013.01); *A61B 2560/0462* (2013.01); *A61B 2562/0219* (2013.01)

(58) Field of Classification Search
CPC ....... A61B 5/4812; A61B 5/11; A61B 5/6831; A61B 5/7264; A61B 5/743; A61B 5/7435; A61B 5/7455; A61B 2560/0214; A61B 2560/045; A61B 2560/0462; A61B 2562/0219; H04M 1/72409; H04M 1/72451; G08B 6/00
See application file for complete search history.

(56) References Cited

U.S. PATENT DOCUMENTS 5,613,498 A * 3/1997 Yasushi .................. A61B 5/375
600/27
9,060,880 B2 * 6/2015 Van Beest ............ A61B 5/4561

(Continued)

*Primary Examiner* — Quang Pham
(74) *Attorney, Agent, or Firm* — Barich IP Law Group

(57) ABSTRACT

A system and method is provided including a wearable alarm system that senses a user's movement during sleep in order to determine the user's sleep state and then awakens the user when the user is experiencing light sleep in order to improve the user's sleep experience. The alarm system receives a latest wakeup time, a user movement threshold trigger, and a begin-analysis time offset and divides the time represented by the begin-analysis time offset into a plurality of intervals. The alarm system uses a wearable accelerometer that compares the user's movement to the predetermined user movement threshold and to determine when a minimum number of threshold movements have been detected in two subsequent time intervals to initiate a haptic and visible alarm to awaken the user.

18 Claims, 15 Drawing Sheets

(56) References Cited

U.S. PATENT DOCUMENTS

| | | | | |
|---|---|---|---|---|
| 9,192,326 | B2 | 11/2015 | Kahn et al. | |
| 9,808,185 | B2 * | 11/2017 | Arnold | A61B 5/1123 |
| 9,809,228 | B2 * | 11/2017 | Hong | B60W 40/08 |
| 9,993,179 | B2 * | 6/2018 | van Beest | A61B 5/1116 |
| 10,235,859 | B1 * | 3/2019 | Hiles | A61B 5/18 |
| 10,485,474 | B2 * | 11/2019 | Kahn | A61B 5/1118 |
| 10,610,153 | B2 * | 4/2020 | Auphan | G01G 19/445 |
| 10,722,147 | B2 * | 7/2020 | Van Oorschot | A61B 5/4818 |
| 11,180,158 | B1 * | 11/2021 | Lyle | B60W 40/08 |
| 11,298,048 | B2 * | 4/2022 | Van Der Hulst | A61B 5/7455 |
| 11,523,770 | B2 * | 12/2022 | Ikoma | A61B 5/4809 |
| 11,553,850 | B2 * | 1/2023 | Lee | A61B 5/681 |
| 12,107,811 | B2 * | 10/2024 | Gamard | H04L 51/21 |
| 12,537,019 | B2 * | 1/2026 | Ostrem | G06V 10/56 |
| 12,593,146 | B2 * | 3/2026 | Van Der Tempel | G01J 1/44 |
| 2006/0125794 | A1 * | 6/2006 | Afriat | G06F 1/32 345/166 |
| 2008/0191885 | A1 * | 8/2008 | Loree, IV | A61B 5/6828 600/595 |
| 2008/0306351 | A1 * | 12/2008 | Izumi | A61B 5/4815 600/300 |
| 2013/0072823 | A1 * | 3/2013 | Kahn | G04G 13/026 600/595 |
| 2013/0208576 | A1 * | 8/2013 | Loree, IV | G04G 11/00 368/256 |
| 2013/0229283 | A1 * | 9/2013 | Receveur | A61B 5/1128 382/103 |
| 2014/0176335 | A1 * | 6/2014 | Brumback | G16H 40/63 340/870.01 |
| 2014/0269223 | A1 * | 9/2014 | Mokhnatkina | G04G 21/025 368/73 |
| 2015/0251074 | A1 * | 9/2015 | Ahmed | A61B 5/02405 700/91 |
| 2015/0359992 | A1 * | 12/2015 | Sudo | A61M 21/00 600/27 |
| 2016/0000359 | A1 * | 1/2016 | Li | A61B 5/742 600/595 |
| 2016/0071393 | A1 * | 3/2016 | Kaplan | G08B 21/06 340/539.12 |
| 2016/0364966 | A1 * | 12/2016 | Dixon | G08B 13/1961 |
| 2017/0231528 | A1 * | 8/2017 | Nathan | A61B 5/4082 600/483 |
| 2017/0355377 | A1 * | 12/2017 | Vijaya Kumar | B60W 50/0098 |
| 2018/0235519 | A1 * | 8/2018 | Franinovic | A61B 5/0004 |
| 2018/0256094 | A1 * | 9/2018 | Russell | A61B 5/02 |
| 2018/0267540 | A1 * | 9/2018 | Sonoura | G05D 1/0088 |
| 2019/0180283 | A1 * | 6/2019 | Unnerstall | A61B 5/4812 |
| 2019/0183427 | A1 * | 6/2019 | Fu | A61B 5/6892 |
| 2019/0220240 | A1 * | 7/2019 | Gan | G10H 1/02 |
| 2019/0318617 | A1 * | 10/2019 | Park | A61B 5/02416 |
| 2019/0365332 | A1 * | 12/2019 | Fedichev | A61B 5/11 |
| 2020/0029890 | A1 * | 1/2020 | Yamanishi | A61B 5/113 |
| 2020/0090488 | A1 * | 3/2020 | Qi | G06Q 30/0215 |
| 2020/0098300 | A1 * | 3/2020 | Verma | G09G 3/2003 |
| 2020/0253547 | A1 * | 8/2020 | Harris | A61B 5/7203 |
| 2021/0338170 | A1 * | 11/2021 | Ochiai | A61B 5/024 |
| 2022/0183618 | A1 * | 6/2022 | Capodilupo | A61B 5/02055 |
| 2022/0273269 | A1 * | 9/2022 | Capodilupo | A61B 10/0012 |
| 2022/0280747 | A1 * | 9/2022 | Shouldice | A61M 21/02 |
| 2022/0287629 | A1 * | 9/2022 | Forsyth | G09G 5/36 |
| 2023/0148956 | A1 * | 5/2023 | Narayanan | A61B 5/4809 600/301 |
| 2023/0200751 | A1 * | 6/2023 | Koskimäki | A61B 5/02416 600/301 |
| 2023/0337971 | A1 * | 10/2023 | Chuang | A61B 5/4809 |
| 2025/0311947 | A1 * | 10/2025 | Napoletano | A61B 5/6823 |
| 2025/0318731 | A1 * | 10/2025 | Atarot | A61B 5/6826 |

* cited by examiner

SLEEP CYCLE-BASED WEARABLE VIBRATION ALARM SYSTEM AND METHOD

CROSS-REFERENCE TO RELATED APPLICATIONS

The present application claims the benefit of U.S. Provisional Application No. 63/523,818, filed Jun. 28, 2023, entitled "Sleep Cycle-Based Wearable Vibration Alarm System and Method", which is hereby incorporated by reference in its entirety.

BACKGROUND OF THE INVENTION

The present invention generally relates to a sleep alarm system. More particularly, the present invention relates to a wearable sleep alarm system that is based on a user's sleep cycle.

Getting good sleep is important to our mood, performance, and health. Sleep is commonly viewed to include five stages: N1, N2, N3, and REM. Stages N1, N2, and N3 are considered non-rapid eye movement (NREM) sleep, with each stage leading to progressively deeper sleep and the lowest sleep state of REM sleep.

One aspect that impacts our experience of our sleep quality is the sleep state in which we are awakened. Generally people awakened in lower sleep states report feeling less rested and experience lowered performance as compared to people awakened in lighter sleep states such as N1 or N2.

BRIEF SUMMARY OF THE INVENTION

One or more of the embodiments of the present invention provide a wearable alarm system that senses a user's movement during sleep in order to determine the user's sleep state and then awakens the user when the user is experiencing light sleep in order to improve the user's sleep experience. The alarm system receives a latest wakeup time, a user movement threshold trigger, and a begin-analysis time offset. The begin-analysis time offset is subtracted from the latest wakeup time to determine an analysis-begin time. The time between the analysis-begin time and the latest wakeup time is divided into a plurality of time intervals. During the time between the analysis-begin time and the latest wakeup time, the alarm system receives accelerometer data from an accelerometer positioned on a user's wrist in order to determine the user's movements. When the user's movement exceeds the user movement trigger, the alarm system determines the current time interval and increments a count of threshold triggers for the current time interval. When the count of threshold triggers for both the current time interval and the previous time interval are at least three, the alarm system activates a haptic and visible alarm to awaken the user.

DETAILED DESCRIPTION OF THE INVENTION

Figure 1:
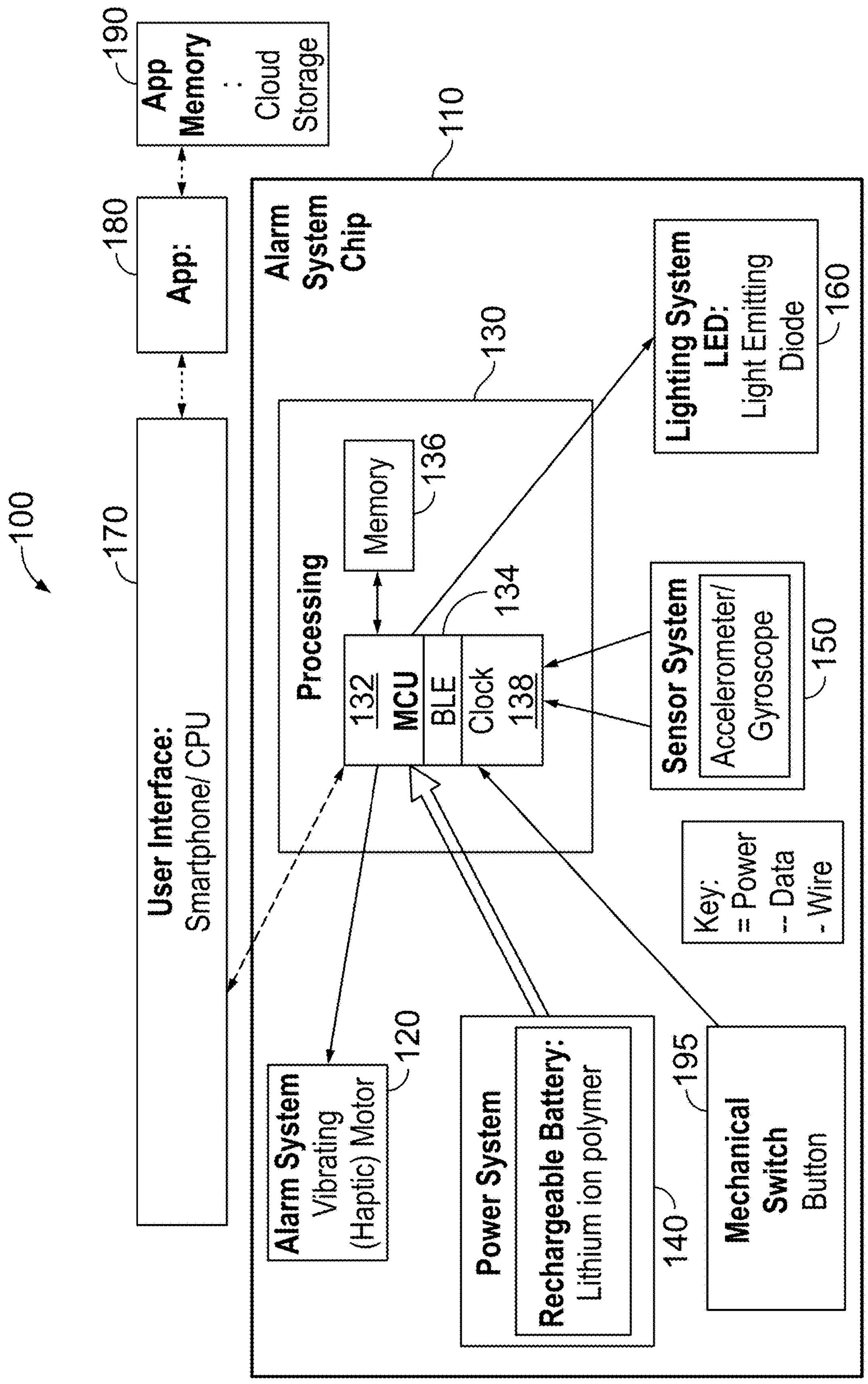
FIG. 1 illustrates a functional block diagram of a sleep cycle-based wearable vibration alarm system according to an embodiment of the present invention.

FIG. 1 illustrates a functional block diagram of a sleep cycle-based wearable vibration alarm system 100 according to an embodiment of the present invention. As shown in FIG. 1, the alarm system 100 includes an alarm system chip 110, a user interface 170, an application 180, and an application memory 190. The alarm system chip 110 includes an alarm 120, a processing system 130, a power system 140, a sensor system 150, a light system 160 and a mechanical switch 195. The processing system 130 includes a Micro-Controller Unit (MCU) 132, a Bluetooth low energy wireless connectivity system (BLE) 134, a memory 136, and a clock 138.

In one embodiment, the user interface 170 may be provided by a smartphone and may use the Central Processing Unit (CPU) of the smartphone in combination with the smartphone's touchscreen. The user interface 170 is in communication with the alarm system chip 110 through the BLE 134. The application 180 may be stored in memory at the smartphone and may be executed by the CPU of the smartphone. The application 180 and smartphone may be in communication with the application memory 190, which may be a cloud-based memory storage system in one embodiment.

At the alarm system chip 110, the power system 140 provides power to the processing system 130 which controls the transmission of power to the other systems on the alarm system chip 110 including the alarm 120, the sensor system 150, and the light system 160. In one embodiment, the alarm 120 may be a vibrating (haptic) motor that is controlled by the processing system 130. In one embodiment, the light system 160 may be a Light-Emitting Diode (LED). In one embodiment, the sensor system 150 may include an accelerometer and gyroscope implemented either as separate sensors or as a single unit. Further, in one embodiment, the power system 140 may be a rechargeable battery such as a lithium-ion polymer battery.

Figure 2:
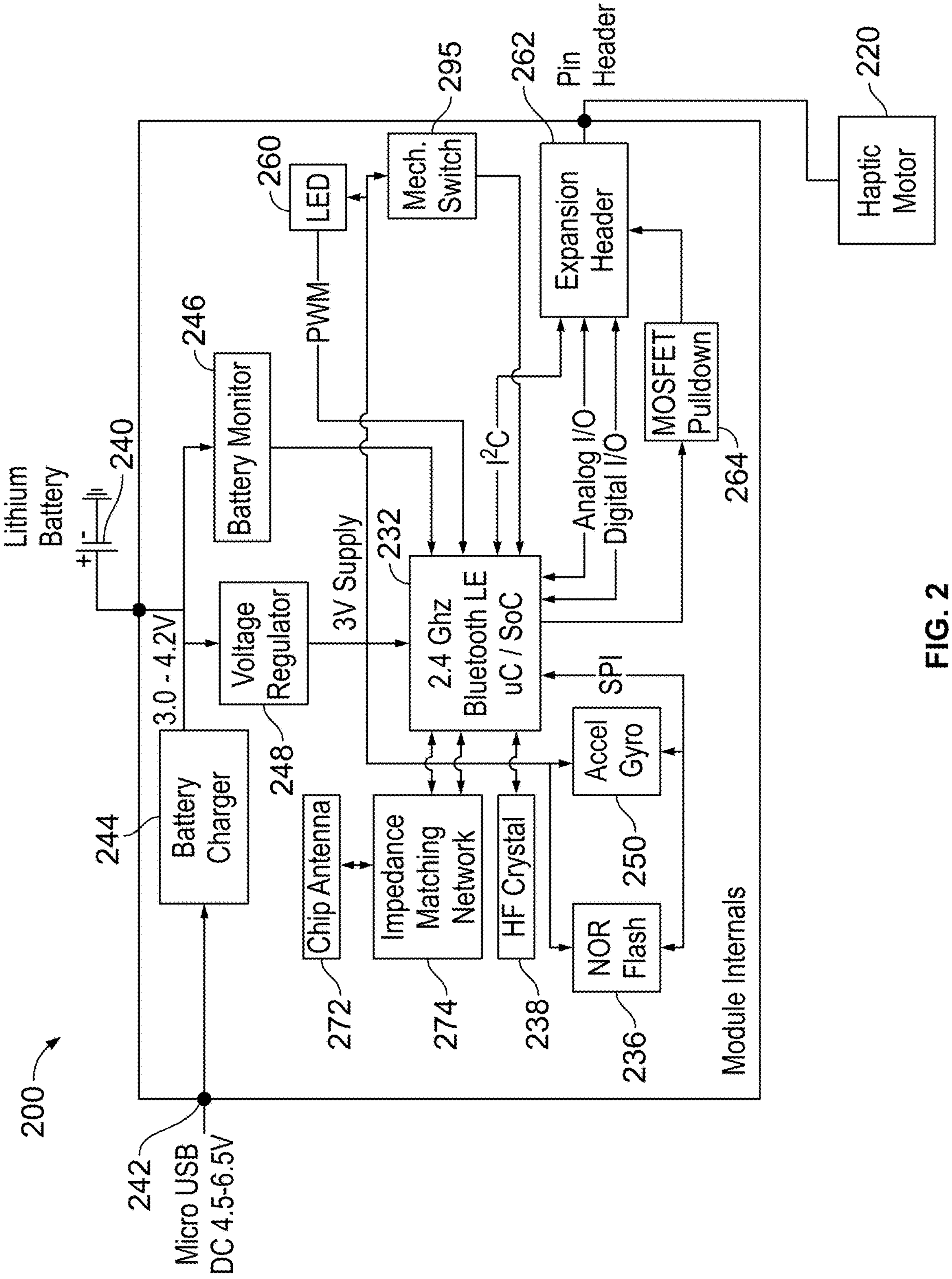
FIG. 2 illustrates a detailed schematic of the alarm system chip of FIG. 1 according to an embodiment of the present invention.

FIG. 2 illustrates a detailed schematic 200 of the alarm system chip 110 of FIG. 1 according to an embodiment of the present invention. The detailed schematic 200 shows an alarm 220 including a haptic motor, a power system 240 including a lithium battery, a sensor system 250 including an accelerometer/gyroscope, a light system 260 including a LED, and a mechanical switch 295. The detailed schematic 200 also shows a processing system including a Bluetooth Low Energy Micro Controller/System On a Chip (SoC) 232 that combines the functionality of a Micro-Controller Unit and Bluetooth low energy wireless connectivity system into one component. Also shown are memory 236 including a NOR Flash memory, and a clock 238 including a High Frequency oscillating crystal. Also shown is a power input 242 for the power system 240, a battery charger 244, a battery monitor 246, and a voltage regulator 248.

In operation, power is received through the power input 242 to charge the power system 240. As shown, the power input 242 may be a Micro-Universal Serial Bus (USB) input. Power received through the power input 242 is passed to the battery charger 244 which charges the power system 240, which may be a lithium battery in one embodiment. The battery monitor 246 monitors the status of the power system 240 and transmits the status to the SoC 232. Power is also provided from the power system 240 to the SoC 232 through the voltage regulator 248 which serves to regulate the voltage supplied to the SoC 232.

As further described herein, the SoC 232 communicates with the memory 236 and sensor system 250 through a Serial Peripheral Interface (SPI).

The SoC 232 also controls the alarm 220 by transmitting an alarm initiation signal through the expansion header 262 to the alarm 220. The MOSFET pulldown 264 operates to prevent undesired activation of the alarm 220.

As shown in FIG. 2, Bluetooth signals are transmitted and received through the chip antenna 272 and pass though the impedance matching network 274 to match the impedance of the chip antenna 272 with the impedance of the SoC 232.

Figure 3:
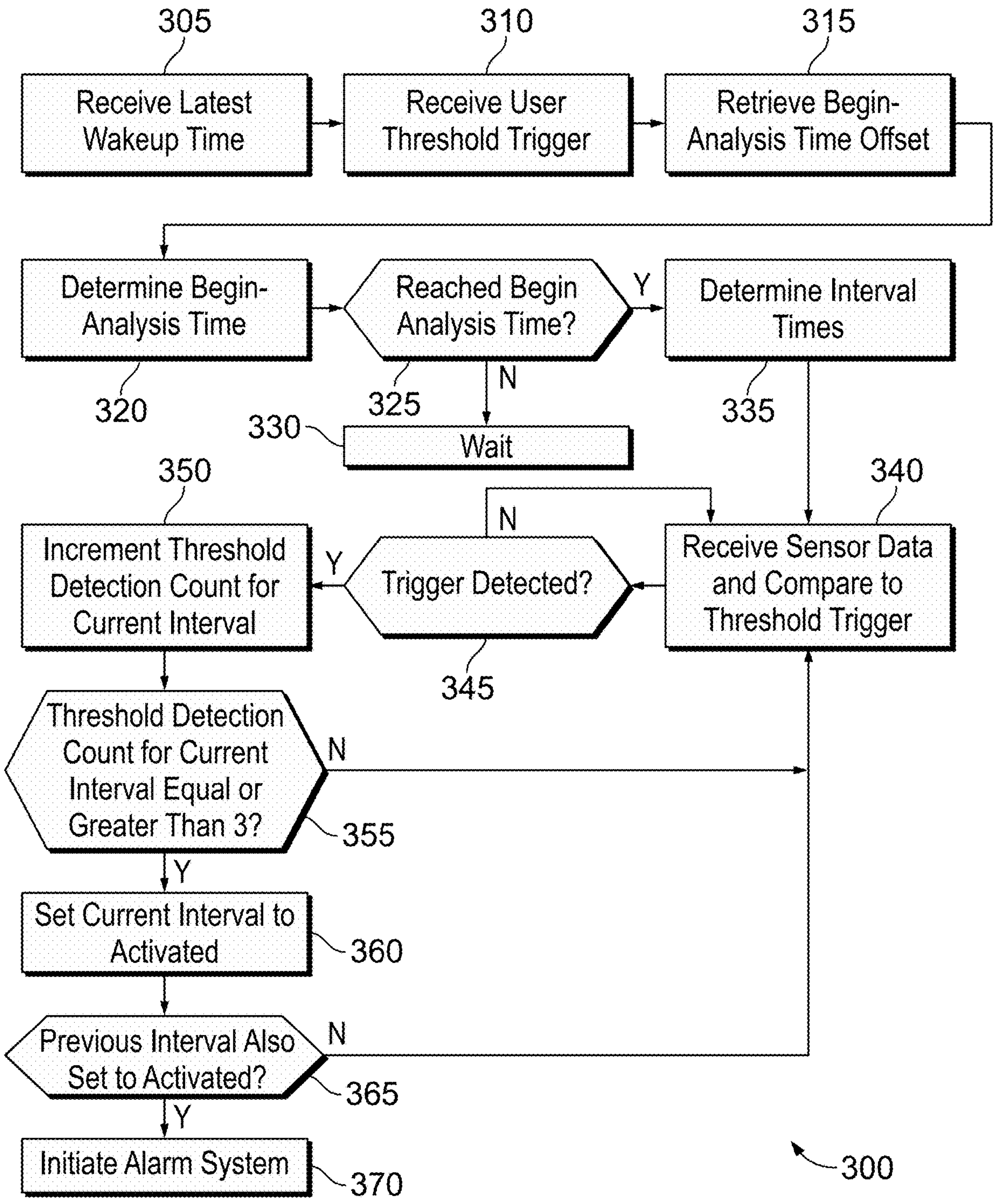
FIG. 3 illustrates a flowchart of the operation of the sleep cycle-based wearable vibration alarm system according to a preferred embodiment of the present invention.

FIG. 3 illustrates a flowchart 300 of the operation of the sleep cycle-based wearable vibration alarm system 100 according to a preferred embodiment of the present invention. First, at step 305, the processing system 130 receives a latest wakeup time from the application 180 that has been entered by the user using the user interface 170. More specifically, the latest wakeup time is transmitted from the application on the smartphone to the chip antenna 272 of the Soc 232 and stored in the NOR Flash memory 236.

The latest wakeup time is a time selected by the user at which the alarm system 100 will initiate an alarm using the alarm system 120 if the alarm system 120 has not yet already been activated.

At step 310, the processing system 130 receives the threshold trigger for the user and stores it in memory 136. More specifically, the threshold triggers may be received from the smartphone application or may be retrieved from the cloud storage application memory 190 by the smartphone application and then passed to the processing system 130.

At step 315, the processing system 130 retrieves the begin-analysis time offset. The begin-analysis time offset may already be previously stored in the memory 136, may be received from the smartphone application 180, or may be retrieved from the application memory 190. The begin-analysis time offset is a length of time prior to the latest wakeup time at which point the processing system 130 will begin to perform its analysis to determine whether to activate the alarm system 120. For example, the latest wakeup time may have been selected to be 8 am and the begin-analysis time offset may be 30 minutes.

At step 320, the processing system 130 subtracts the time offset from the latest wakeup time to determine the time to begin analyzing accelerometer data. For example, for a latest wakeup time of 8 am and a begin-analysis time offset of 30 minutes, the processing system 130 determines that analysis of the accelerometer data will begin at 7:30 am. This time is also stored in the memory 136.

Next, the processing system 130 compares the current time to the begin-analysis time at step 325. For example, the current time may be provided by the clock 138 which may be a high-frequency oscillating crystal 238. When the current time has not yet reached the analysis-begin time, the processing system 130 simply waits, as shown in step 330.

Conversely, when the current time has reached the analysis-begin time, the flowchart proceeds to step 335 and the processing system 130 retrieves from the memory 136 the number of intervals into which to divide the begin-analysis time offset. In one embodiment, the number of intervals may be 15. In another embodiment, the number of intervals may be received from the smartphone application 180 or may be received from the cloud storage based application memory 190. For example, then the begin-analysis time offset is 30 minutes, the number of intervals is 15, and the latest wakeup time is 8 am, the processing system 130 divides the 30 minutes from 7:30 am to 8 am into 15 intervals of 2 minutes each.

Next, at step 340, the processing system 130 receives sensor data from the sensor system 150 and compares the acceleration data from the sensor system 340 to the user's threshold trigger. In one embodiment, the user's threshold trigger may be 1.2 $m/s^2$. In other embodiments, the user's threshold trigger may be in the range of 1.15-1.25 $m/s^2$.

When the acceleration data from the sensor system 340 exceeds the threshold trigger, the processing system 130 detects a trigger at step 345 and the process proceeds to step 350. Conversely, the acceleration data from the sensor system 340 does not exceed the threshold trigger, then the processing system does not detect a trigger and the flowchart proceeds back to step 340.

At step 350, the processing system 130 determines the time at which the current trigger has been detected and then determines which interval the current time falls in. The processing system then increments a trigger detection count that is stored in the memory 136 for each individual interval. The flowchart then proceeds to step 355 wherein the processing system compares the trigger detection count for the current interval to three. When the trigger detection count for the current interval is less than three, the flowchart proceeds back to step 340 and simply receives new sensor data.

Conversely, when the trigger detection count for the current interval is equal to or greater than three, the flowchart proceeds to step 360 and the processing system 130 sets an activated status indicator for the current interval to “activated”, if the activated status indicator has not already been set to “activated”. However, if the activated status indicator is already set to “activated”, then the processing system 130 takes no action. The activated status indicator for each interval is stored in the memory 136 and is initially set to “not activated” for all intervals. Although in one embodiment, the number of trigger detection counts required for the current interval to be set to “activated” is three, a different number such as two, four, or five may be utilized. Additionally, the number of detection counts required for the current interval to be set to activated may be user-selected using the smartphone application or may be retrieved from the cloud-based application memory.

The flowchart then proceeds to step 365 wherein the processing system 130 retrieves the activated status indicator for the previous interval from the memory 136. In one embodiment, the intervals may be numbered sequentially. The processing system 130 may determine the current interval by comparing the current time received from the clock 138 to the start times of the 15 intervals previously determined by the processing system and stored in the memory 136. The activated status indicator for the previous interval may then be identified by decrementing the interval number of the current interval and retrieving the activated status indicator associated with the determined interval.

In one embodiment, when the activated status indicator of the previous interval is not set to “Activated”, the flowchart proceeds back to step 340 and simply awaits new sensor data. Conversely, when the activated status indicator of the previous interval and the current interval are both set to “activated”, then the flowchart proceeds to step 370 and the processing system 130 transmits an alarm activation signal to the alarm system 120 to activate the alarm. The processing system 130 also transmits a signal to the lighting system 160 which causes an LED light to flash.

In operation, in one embodiment, the present sleep cycle-based wearable vibration alarm system 100 is a wearable device that is worn during sleep and acts as an alarm clock. As described herein, the sleep cycle-based wearable vibration alarm system 100 uses accelerometer data to determine when a user is experiencing light sleep rather than REM or deep sleep, for example during the last 30 minutes before the user’s latest wakeup time, and then initiates an alarm during light sleep. Users may be awakened during light sleep because users awakened during light sleep feel less groggy and more well-rested than users awakened during REM or deep sleep.

The sleep cycle-based wearable vibration alarm system 100 may be controlled through the smartphone application 180 which may receive user input through the user interface 170 and may transmit and receive data from both the cloud-based application memory 190 and the alarm system chip 110. As mentioned above, the smartphone application 180 may communicate with the alarm system chip 110 using Bluetooth wireless connectivity and may communicate with the cloud-based application memory 190 using wi-fi or cellular data.

The portion of the sleep cycle-based wearable vibration alarm system 100 that may be positioned on the user’s body may include two components: first, a fabric wristband having a pocket for receiving the alarm system chip 110, a second, the alarm system chip 110 itself. In one embodiment, the alarm system chip 110 is about 8 mm thick and includes an accelerometer, microcontroller, and memory that are used to measure wrist movements while the user sleeps. The microcontroller tells the accelerometer to read raw acceleration data in meters per second squared ($m/s^2$) of the sleeper’s wrist movements and record it to the memory. Once a light sleep stage (NREM1 or NREM2) is detected by wrist movements hitting the stored threshold (which includes magnitude of movement and total number of movements stored in the smartphone application memory and in the memory of the alarm system chip), the microcontroller automatically sends a signal to direct power from the battery to the vibrating motor and start the vibration to wake up the sleeper. The vibrating motor vibrates inside the band on the wrist of the sleeper while a green light blinks on the alarm system chip, gently alerting the user to wake up and visually indicating it is time to rise. The user may then turn off the alarm using a mechanical switch 195 such as a button on the alarm system chip 130, or may enter a command through the user interface 170 to cause the smartphone application 180 to transmit a turn-off command to the alarm system chip 110.

The sleep cycle-based wearable vibration alarm system 100 may thus help users wake up according to their sleep cycle by enabling them to wake up in light sleep (Non-REM or non-deep sleep). This may be especially helpful to people who are particularly sensitive to sleep disturbances, because waking up during REM or deep sleep may be challenging and may result in grogginess, lethargy, and slow cognitive and motor functions. This may be because during REM or deep sleep our brains go through memory consolidation and formation. Interrupting these processes may have negative effects on our mental and physical energy, decision-making abilities, and overall cognitive function. The sleep cycle-based wearable vibration alarm system 100 ensures that individuals are awakened during light sleep, avoiding interference with these crucial and natural brain processes that occur during our deeper sleep (REM and Deep Sleep). The sleep cycle-based wearable vibration alarm system 100 also provides a touch-based alarm system by using the haptic motor, which may be especially helpful to those who are hard of hearing or deaf and thus not able to be awakened using audible alarms.

In one embodiment, the alarm system chip 110 only needs to receive the latest wake up time input from the smartphone application because the user threshold trigger may have been previously stored in the memory on the alarm system chip 110. Thus, after receiving the latest wakeup time, the smartphone no longer is required to be in communication with the alarm system chip 110 and may even be turned off.

Because the alarm system chip 110 includes a clock component which keeps time, the alarm system chip 110 knows how much time passes and does not need to be connected to a smartphone throughout the night. The alarm system chip 110 is a local device, meaning it does not need an internet connection to function but is also not limited to only using Bluetooth wireless connectivity.

In one embodiment, the accelerometer data which is read, stored, and saved on the alarm system chip 110 may be sent back to the smartphone application. More specifically, when the smartphone application establishes communication with the alarm system chip 110, the smartphone application may download the data stored in the memory of the alarm system chip including accelerometer data. The download of data from the alarm system chip 110 to the smartphone application 180 may take place automatically or in response to a download command received at the smartphone application 180 from the user interface 170. Additionally, data that is received at the smartphone application may then be transmitted to the cloud-based application memory 190 for remote storage and potential later retrieval using the smartphone application.

In one embodiment, individual users using the sleep cycle-based wearable vibration alarm system 100 may have a unique threshold trigger. In one embodiment, the Threshold Trigger (TT) is determined from the Average Magnitude of Sleep (AMS) for a user, or how much an individual moves during the night. This is important because everybody has unique movement magnitude of movement and total number of movements at night. To calculate this, sleep cycle-based wearable vibration alarm system 100 first determines what the duration of a user's sleep cycle is, the start and the finish. This is done by identifying the time of onset of REM sleep and counting a new cycle after a REM phase has completed. The REM sleep stage, the deepest stage of sleep, also known as "dream sleep," can be identified by the sleep cycle-based wearable vibration alarm system 100 using the accelerometer as constant 1.0 $m/s^2$ (or less) for longer than 10 min. This is due to the fact that during REM sleep, our bodies are paralyzed to limit movement during our dreams. A new sleep cycle is considered to start after REM sleep completes. The sleep cycle-based wearable vibration alarm system 100 then calculates the average magnitude of sleep (AMS) during each sleep cycle which is the average of how much someone moves at night. This is done by taking the total amount of recorded movement above 1.0 $m/s^2$ and dividing it by the amount of time that has passed during the sleep cycle. The movement data while measuring sleep cycle length and AMS are stored in the memory of the alarm system chip 110 and then transmitted wirelessly to the smartphone application 180 where it is stored in memory and may be further transmitted to the cloud-based application memory 190.

A Threshold Trigger (TT) unique to individuals may then be determined by multiplying the base threshold trigger by 0.8×-1.2× depending on whether the individual has a lower or higher AMS. In one embodiment, the user's AMS may be received and displayed on the user interface 170 as well as an average AMS. The multiplier for the base threshold trigger may also be displayed and adjusted through the user interface 170 for the smartphone application 180. In one embodiment, when the user's AMS is higher than the average AMS, then a lower multiplier such as 0.8 may be applied to obtain the user's threshold trigger. Conversely, when the user's AMS is lower than the average AMS, then a higher multiplier such as 1.2 may be applied to obtain the user's threshold trigger. The personalization of the multiplier may be adjusted through using the user interface 170 of the smartphone application 180 and the new personalized threshold trigger may then be transmitted to the alarm system chip 110 through the Bluetooth enabled connection 134 and stored in the memory 136. By personalizing the TT using the AMS, the user's specific threshold trigger may be adapted to each individual's unique movements. This results in the sleeper waking up at the conclusion of their REM sleep, in light sleep resulting in a more natural and gentle wake up experience.

In one embodiment, the average magnitude of a sleep cycle is measured once an individual starts entering sleep (Hypnic Jerks) ending with the Alarm Triggered (AT) to minimize sleep movement noise. Sleep movement noise refers to the movement that happens before falling asleep whilst the person is not yet sleeping or is waking up (for example, walking around, being active, or reading).

Figure 4:
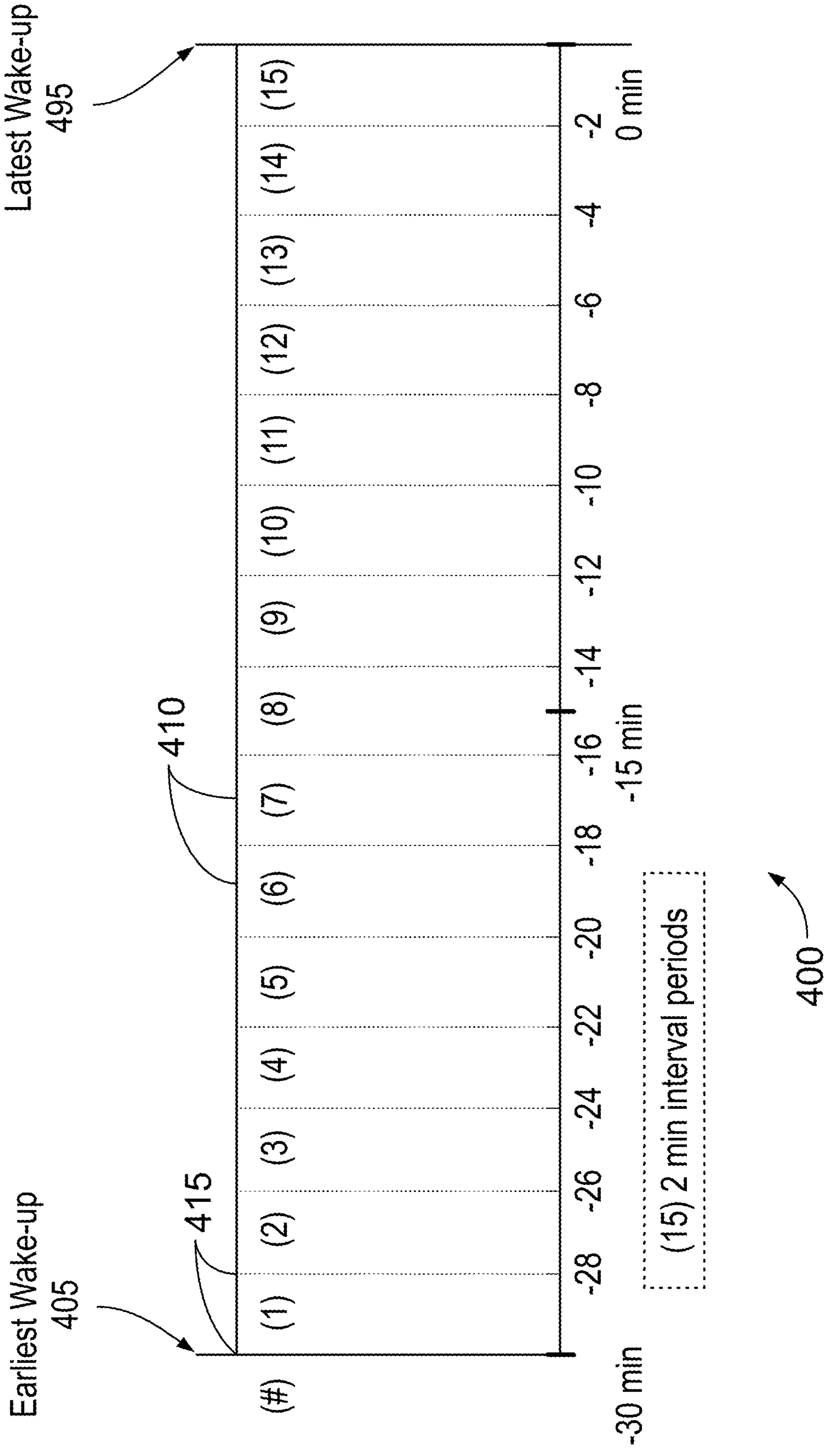
FIG. 4 is a representation of the construction of the time intervals as mentioned in FIG. 3.

FIG. 4 is a representation of the construction of the time intervals as mentioned in FIG. 3, step 335 above. As described above, the latest wakeup time 495 has previously been received from the smartphone application 180 and stores in the memory 136. The processing system 130 then applies the predetermined time offset (for example, 30 minutes) to determine the earliest wakeup time 405. The processing system then applies the predetermined number of intervals (for example 15) to divide the time between the earliest wakeup time 405 and the latest wakeup time 495 into 15 uniform time intervals 410 (for example, of 2 minutes each). In one embodiment, the time intervals are numbered sequentially as shown in FIG. 4 and a data structure is established in the memory 136 that includes an entry for each interval as well as the start time for each interval and a threshold detection count for each interval, which is initially set to zero.

The earliest wakeup time 495 is theoretically the earliest time at which the processing system 130 may initiate the alarm system 120 and lighting system 160. However, because the initiation of the alarm system 120 requires the detection of at least three triggering events of the user's accelerometer readings exceeding the user's threshold, and those triggering events are not monitored until the earliest wakeup time 405 is initiated and may take a finite amount of time to occur, the earliest wakeup time may also be known as the monitoring start time.

Conversely, the latest wakeup time 495 is the time at which the processing system 130 will initiate the alarm system 120 and lighting system 160, even if no triggering events have been detected.

Figure 5:
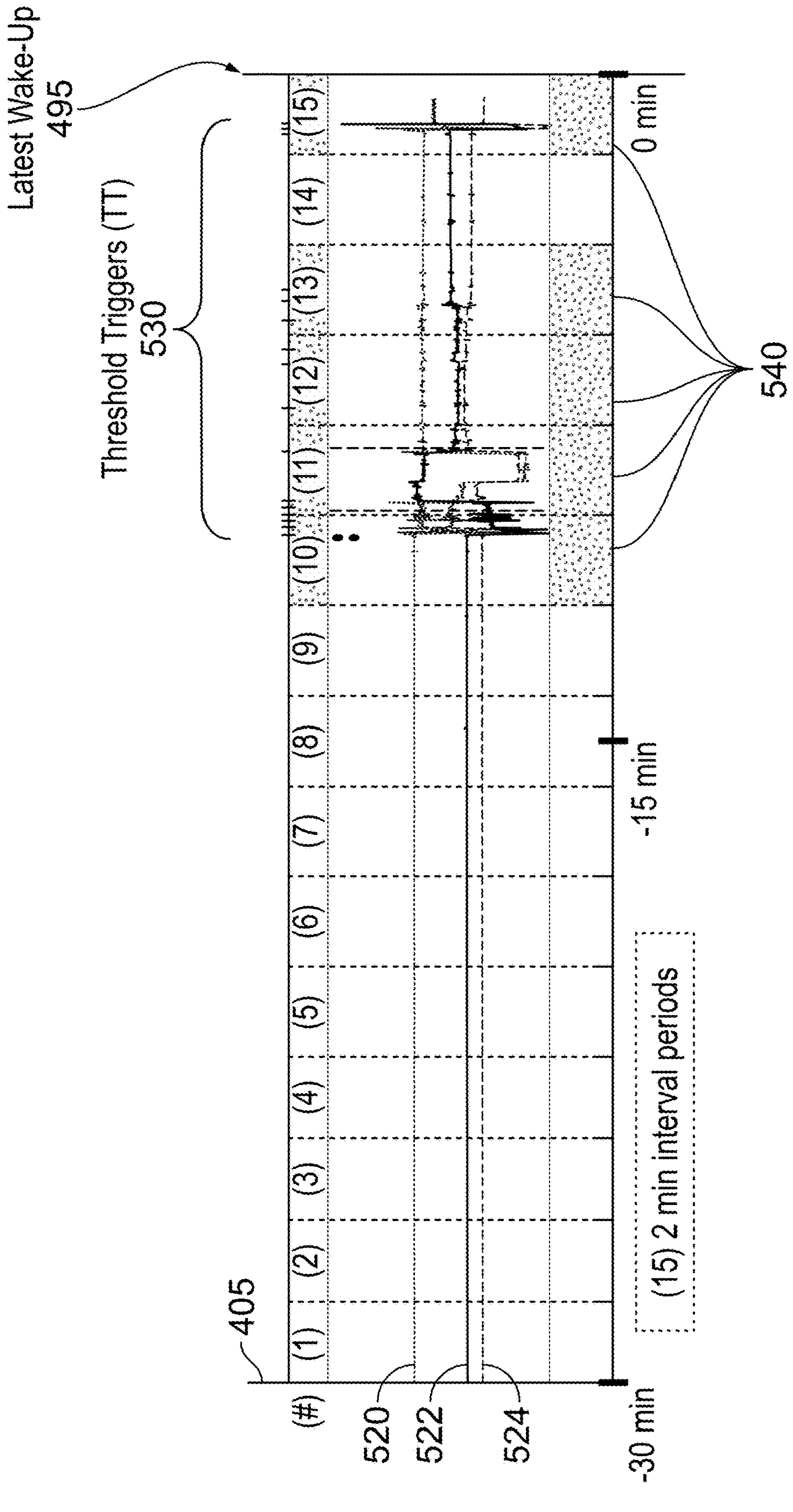
FIG. 5 is a representation of the receiving sensor data from the sensor system during the time intervals constructed in FIG. 4.

FIG. 5 is a representation of the receiving sensor data from the sensor system 150 during the time intervals constructed in FIG. 4. More specifically, in FIG. 5 the sensor system 150 includes three-dimensional accelerometer data. As mentioned above, the alarm system chip 110 maybe affixed to the wrist of a user and the three dimensional accelerometer data may be used to track the position and orientation of the accelerometer as the user move. Thus, FIG. 5 shows accelerometer data for the X dimension 520, Y dimension 522, and Z dimension 524 over time as measured in $m/s^2$.

As shown in earlier intervals 1-9, the accelerometer data 520-524 is relatively constant indicating that the orientation of the accelerometer is not changing. However, in interval 10, the accelerometer data 520-524 is shown to change significantly as the user moves their wrist and the accelerometer attached to the user's wrist moves in response.

The three-dimensional accelerometer data 520-524 is summed and passed through a RMS (root-mean-squared) filter starting at the earliest wakeup time 405 until the latest wakeup time 495. When the summed, RMS accelerometer data exceeds the user's threshold trigger, the processing system 130 detects that the threshold has been exceeded, as mentioned in step 345 of FIG. 3 and increments the threshold detection count for the current interval that is stored in the memory 136. As mentioned above, the user's threshold may be a fixed 1.2 $m/s^2$ or may be adjustable by the user in the range of 1.15-1.25 $m/s^2$.

FIG. 5 provides a graphical illustration of when the processing system 130 has detected that the threshold has been exceeded by indicating a vertical hash mark 530 along the top horizontal edge of the interval chart. As mentioned above in FIG. 3, then the processing system detects that the threshold has been exceeded three or more times in the current interval, the current interval is set to "activated" in the memory 136. As shown in FIG. 5, intervals 10, 11, 12, 13, and 15 have at least three detected instances where the threshold has been exceeded and are thus set as activated intervals 540 in the memory 136.

Figure 6:
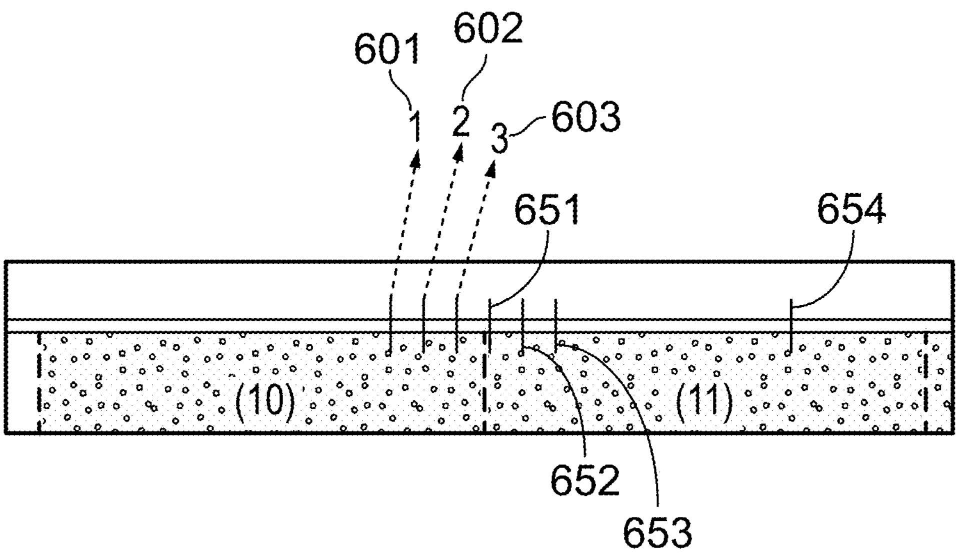
FIG. 6 illustrates a close up view of the vertical hash marks indicating the detection that the threshold has been exceeded.

FIG. 6 illustrates a close up view of the vertical hash marks 530 indicating the detection that the threshold has been exceeded. As shown in FIG. 6, three instances where the user's threshold has been exceeded 601, 602, 603 have been detected in interval 10. Thus, interval 10 is set to activated in the memory 136. Similarly, as shown in FIG. 6, four instances where the user's threshold has been exceeded are shown in interval 11 (651, 652, 653, 654). When the third instance 653 was detected, interval 11 was set to activated in the memory 136. When the additional fourth detection 654 occurs, the processing system 130 determines that interval 11 has already been set to activated and consequently take no action with regard to setting the interval as activated.

Figure 7:
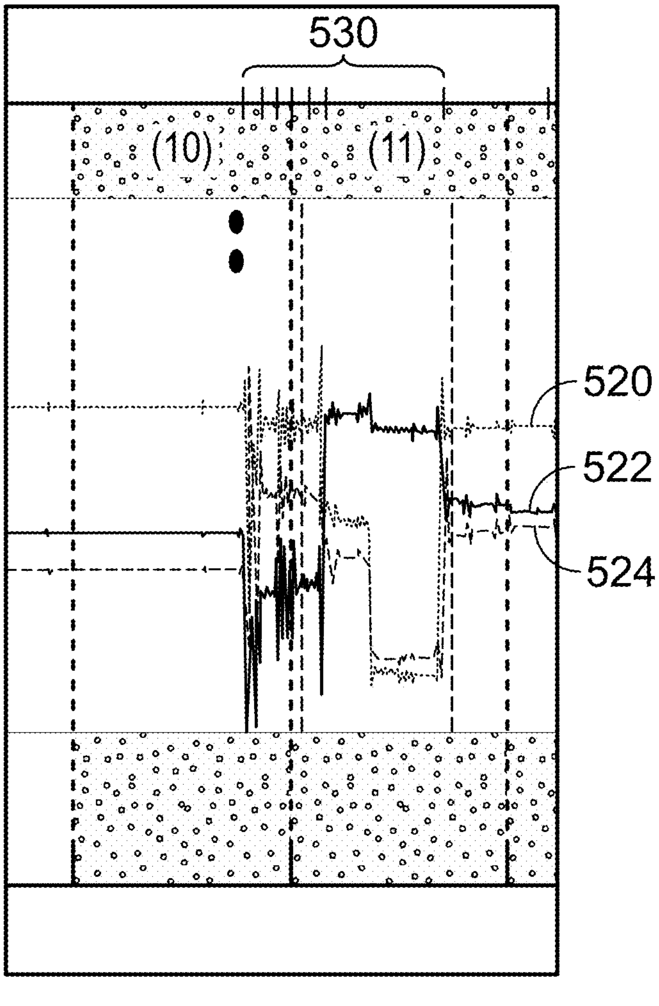
FIG. 7 illustrates a closeup view of activated intervals 10 and 11 showing both the threshold triggers and the three dimensional accelerometer data.

FIG. 7 illustrates a closeup view of activated intervals 10 and 11 showing both the threshold triggers 530 and the three dimensional accelerometer data 520-524.

Figure 8:
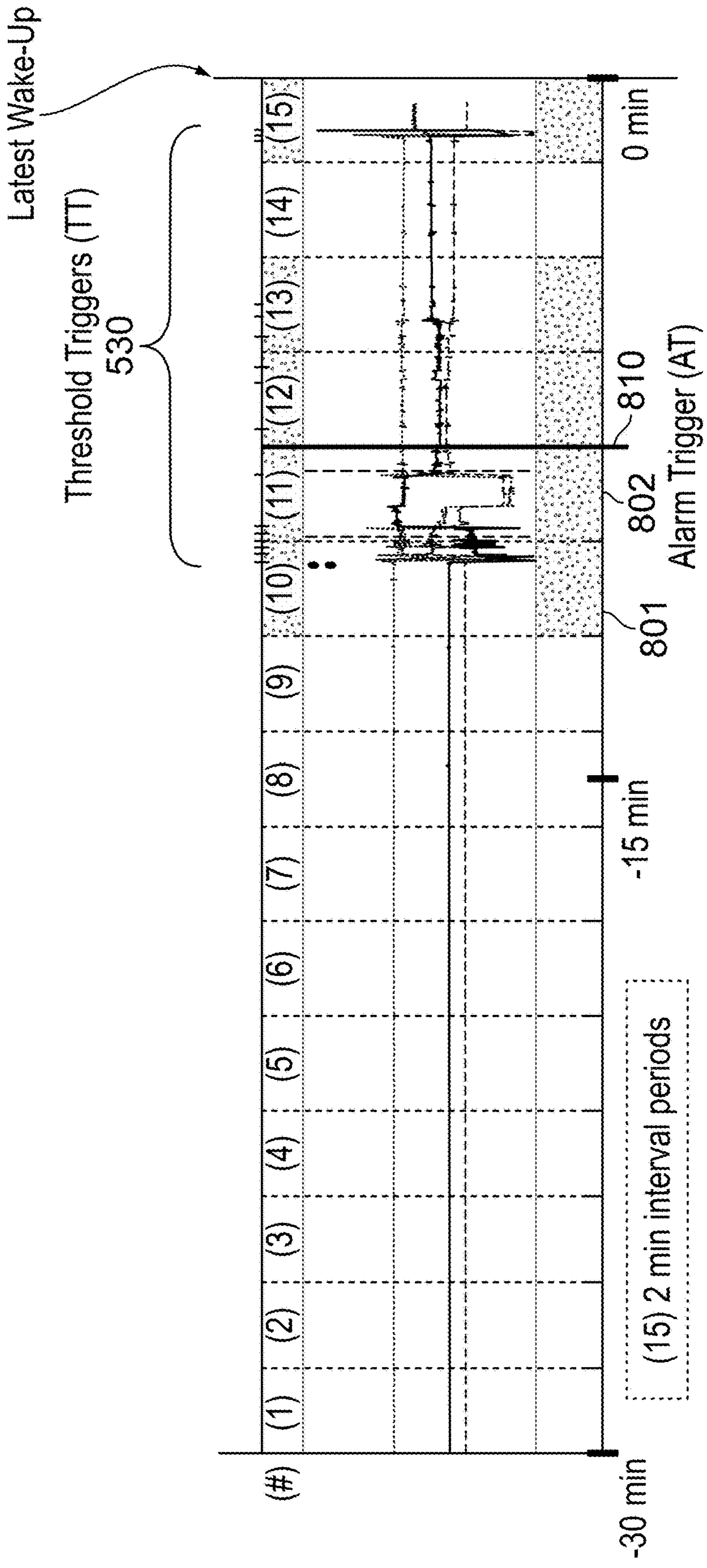
FIG. 8 illustrates the alarm system being triggered in response to the detection of the two activated intervals.

FIG. 8 illustrates the alarm system being triggered in response to the detection of the two activated intervals. As mentioned above, intervals 10 and 11 are activated intervals because at least three threshold triggers 530 where the user's threshold has been exceeded has been detected in each interval. Interval 10 thus forms a first activated interval 801 and interval 11 is a second activated interval 802. As shown in FIG. 8 at the time of the end of the second activated interval 802 (which is also the start time of interval 12), the processing system may initiate the activation of the alarm system 120 and lighting system 160 in order to awaken the user.

Interval activation may also occur when a user is in Deep Sleep (Stage N3) due to sleep jerks or other movements, so in order to ensure that the sleeper is in the Light Sleep Stage (N1-N2), alarm system activation takes place after two consecutive Interval Activations (IA).

In another embodiment, the alarm system 120 and lighting system 160 may be activated immediately upon the detection of the third threshold trigger in interval 11 (second activated interval 810) instead of at the end of the second activated interval 810.

Figure 9:
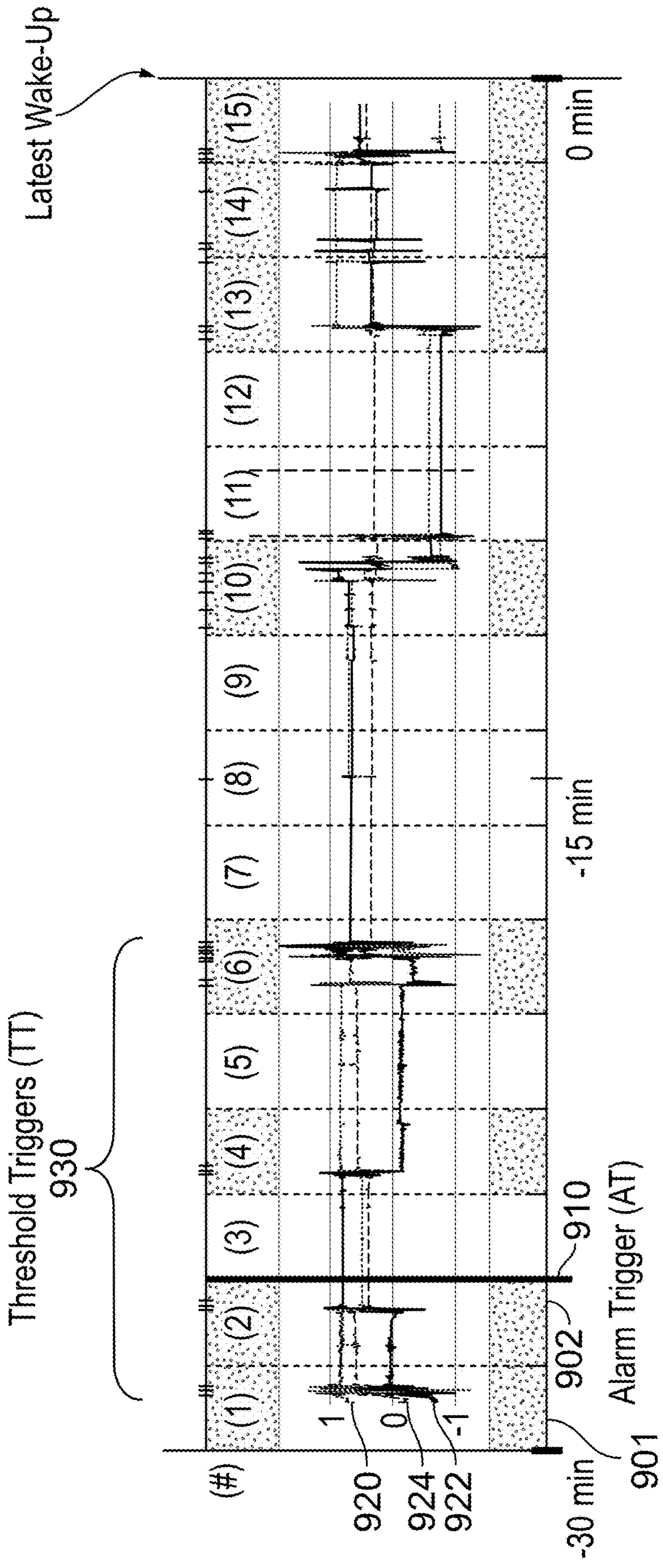
FIG. 9 illustrates a different embodiment of sensor system data being evaluated by the processing system.

FIG. 9 illustrates a different embodiment of sensor system data being evaluated by the processing system 130. In FIG. 9, new three-dimensional accelerometer data is provided for the X-dimension 920, Y-dimension 922, and Z-dimension 924. The new accelerometer data may represent a different user from FIG. 8 above or may represent the activity of the same user on a different night. As described above, the processing system 130 monitors the acceleration data and determines when the acceleration data exceeds the user's threshold trigger. The temporal points at which the processing system determines that the user's threshold has been exceeded are indicated by vertical hash marks 930.

As shown in FIG. 9, three threshold detections have taken place in the first interval. Thus, interval 1 is set as a first activated interval 901. Similarly, three threshold detections have taken place in the second interval 902. Thus, interval 2 is set as a second activated interval. Finally, because both interval 1 and interval 2 are activated intervals, the processing system initiates the alarm system 120 and lighting system 160 as the end of interval 2/start of interval 3.

Conversely, if interval 2 had not included three threshold detections, interval 2 would not be an activated interval. In one embodiment, the present system requires two activated intervals to take place in succession in order for the alarm system to be activated. Consequently, even if interval 1 had been activated, if interval 2 had not been activated, then the alarm system 120 would not have been initiated at the end of interval two. Instead, the processing system would simply continue to monitor the three dimensional acceleration data 920-924 until two successive activated intervals take place, which would occur with intervals 12 and 14. Consequently, the alarm system 120 and lighting system 160 would be activated at the end of interval 14/start of interval 15.

Figure 10:
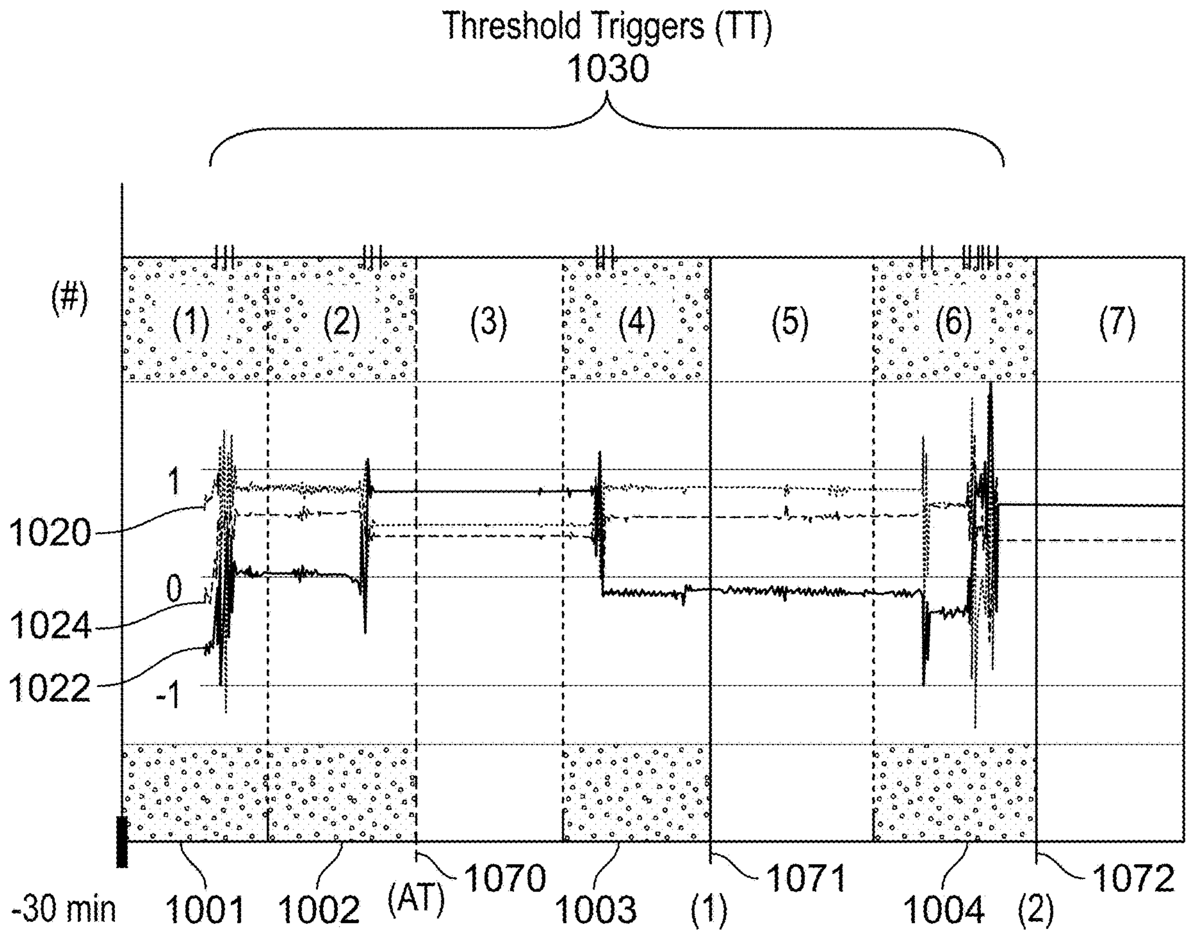
FIG. 10 illustrates the smart snooze operation according to an embodiment of the present invention.

FIG. 10 illustrates the smart snooze operation according to an embodiment of the present invention. As shown in FIG. 10, intervals 1, 2, 4, and 6 have recorded at least three threshold triggers 1030. Thus, interval 1 is a first activated interval 1001, interval 2 is a second activated interval 1002, interval 4 is a third activated interval 1003, and interval 6 is a fourth activated interval 1004. In operation, the smart snooze operation allows a user to postpone the activation of the alarm system 120 from the alarm system's typical activation at the end of the second subsequent activated interval until the expiration of the next subsequent activated interval (which represent the user's next subsequent Light Sleep period.) The smart snooze operation may be useful because after 7-8 hours of sleep the user may alternate between Light Sleep and REM. Users may wake up briefly in Light Sleep, but still feel an urge to continue sleeping. In these cases, in order to give the user some extra REM sleep, if a user chooses to snooze, they will be woken up at their next light sleep period, or IA, within the total 30-min time window. Even if no subsequent activated interval is detected, the alarm system 120 is still activated at the latest wakeup time.

As shown in FIG. 10, typically after the first activated interval 1001 is followed by the second activated interval 1002, the alarm would be triggered at the alarm trigger 1070 point at the end of the second interval/start of the third interval. However, a user may then initiate smart snooze operation by selecting smart snooze through the user interface 170 of the smartphone application 180, which is then transmitted to the processing system. Alternatively, the user may select smart snooze by activating the mechanical switch 195 such as a button positioned on the alarm system chip 130.

Once the smart snooze is activated, if the alarm system 120 and lighting system 160 have already been activated due to two successive activated intervals taking place, the alarm system 120 and lighting system 160 are deactivated. The processing system 130 then continues to monitor the three dimensional accelerometer data 1020-1024 and determines when the next subsequent threshold triggers take place and then determines the next activated interval. As shown in FIG. 10, the next activated interval after interval 2 is interval 4, which is the third activated interval 1003 because three threshold triggers 1030 have taken place in that interval. Consequently, the processing system 130 causes the alarm system 120 and lighting system 160 to be activated at the end of the third activated interval 1003/start of interval 5.

If a user again activated the smart snooze operation, the processing system 130 again deactivates the alarm system 120 and lighting system 160 and continues to monitor the three dimensional accelerometer data 1020-1024 and determines when the next subsequent threshold triggers take place and then determine the next activated interval. As shown in FIG. 10, the next activated interval after interval 4 is interval 6, which is the fourth activated interval 1004 because three threshold triggers 1030 have taken place in that interval. Consequently, the processing system 130 causes the alarm system 120 and lighting system 160 to be activated at the end of the fourth activated interval 1004/start of interval 7.

Figure 11:
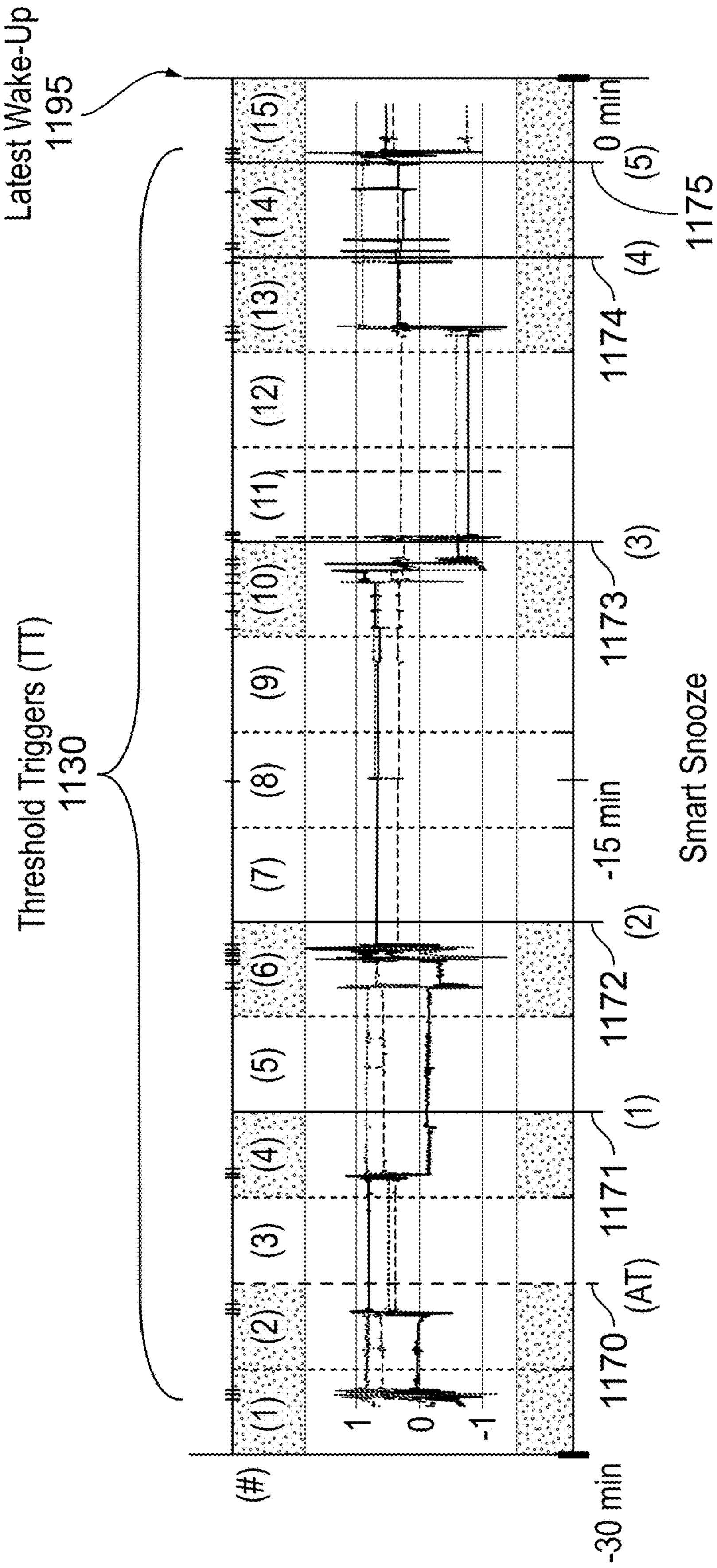
FIG. 11 illustrates the smart snooze operation on over a full 30 minute offset.

FIG. 11 illustrates the smart snooze operation on over a full 30 minute offset. As shown in FIG. 11, highlighted intervals are activated intervals because at least three threshold triggers 1130 have taken place in that interval. As shown in FIG. 11, activated intervals include intervals 1, 2, 4, 6, 10, 13, 14, and 15. Under normal operation, intervals 1 and 2 are activated intervals that are subsequent to each other and thus an alarm is triggered at alarm trigger time 1170 at the end of the second interval.

However, if a user selects smart snooze, the alarm is deactivated and the processing system waits for the next activated interval to again activate alarm system 120 and lighting system 160. The next subsequent activated interval is interval 4 which ends at first snooze time 1171. Similarly, if smart snooze is again activated, the processing system deactivates the current alarm and waits until the end of the next activated interval, which is interval 6, at second snooze time 1172. If smart snooze is activated again, the processing system waits until the end of the next activated interval, which is interval 10 at third snooze time 1173. If smart snooze is activated again, the processing system waits until the end of the next activated interval, which is interval 13 at fourth snooze time 1174. If smart snooze is activated again, the processing system waits until the end of the next activated interval, which is interval 14 at fifth snooze time 1175. Finally, at the latest wakeup time 1195, the alarm system 120 and lighting system 160 are activated and no snooze operation is allowed. As can be seen in FIG. 11, the next subsequent activated interval may be multiple intervals away (such as the difference between interval 6 and interval 10) or may be the next subsequent interval (such as the difference between interval 13 and 14.)

Figure 12:
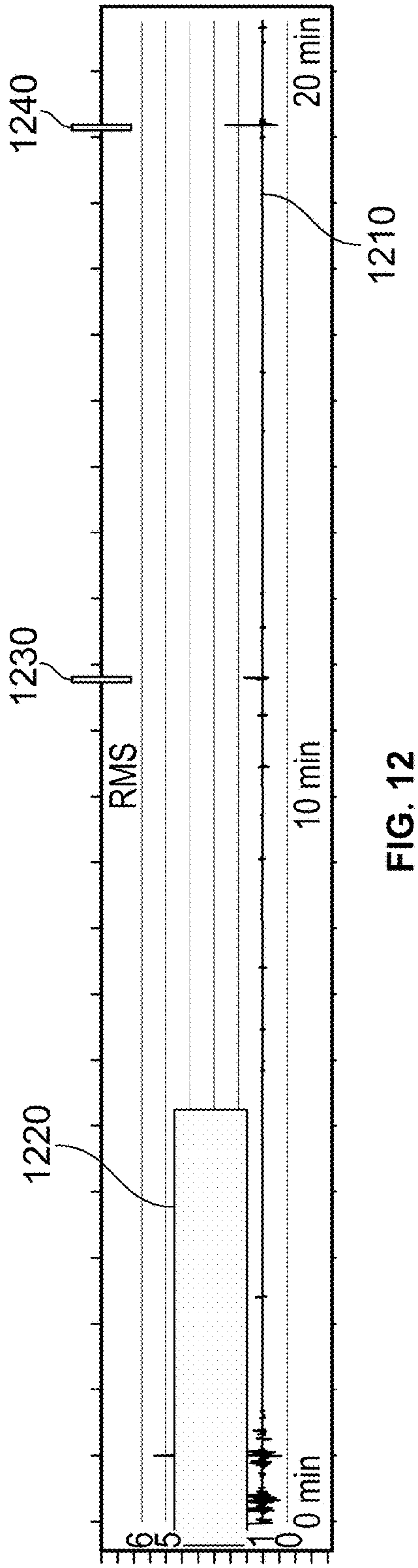
FIG. 12 illustrates a power nap operation according to an embodiment of the present invention.

FIG. 12 illustrates a power nap operation according to an embodiment of the present invention. To initiate the power nap operation, a user may select a power nap using the user interface 170 of the smartphone application 180 which transmits the instructions to start the power nap to the alarm system chip 110. The power nap is set to last for 20 minutes. During the first 5 minutes, the processing system does not collect and save to memory the accelerometer data, thus forming a blackout period 1220 as shown in FIG. 12. This is because it generally takes 5 minutes for users to initiate napping so the alarm system chip 110 ignores the first 5 minutes.

After 5 minutes, the alarm system chip 110 starts to collect raw acceleration data in $m/s^2$. If the absolute value of the RMS (root-mean-squared) of the acceleration exceeds 1.5 $m/s^2$ it is considered a Hypnic Jerk Trigger. If a Hypnic Jerk is detected, the alarm system 110 starts the Power Nap wake-up process. During this process, the alarm system 110 first waits 90 seconds and then proceeds to send a signal to the battery to power the alarm system's 120 vibrating motor and may also activate the lighting system 160. The alarm system 110 may then be turned off using either the mechanical switch 195 which may be a button or by using the user interface 170 or the smartphone application 180. The alarm system 110 automatically starts to vibrate after 20 minutes if no hypnic jerk triggers have been detected.

FIG. 12 shows the blackout period 1220 as well as the RMS value of the three-dimensional acceleration data received from the sensor system 150 accelerometer. Also shown are the first hypnic jerk trigger 1230 and second hypnic jerk trigger 1240.

The power nap operation allows the present system to be used for a quick rejuvenating nap. During this short nap (10-20 minutes, the length of which may be selected by the user using the user interface) the accelerometer, the chip memory, and the microcontroller all work to measure the raw acceleration of the wrist (in $m/s^2$). Once the microcontroller reads a trigger above a set value (1.5 $m/s^2$), the microcontroller starts the Power Nap wake-up process. The Power Nap wake-up process starts with a 90 second pause and then proceeds to turn on the vibrating motor. The alarm system chip 110 wakes the user from a short but effective power nap.

Additionally, the trigger value associated with a Hypnic Jerk may be unique to each individual and may be determined based on an individual's average magnitude of movements during the night. Similar to as discussed above with regard to adjusting the Threshold Trigger to be unique to individuals, the trigger value associated with the Hypnic Jerk may also be adjusted by multiplying the base Hypnic Jerk trigger by 0.8×-1.2× depending on whether the individual has a lower or higher AMS. In one embodiment, the user's AMS may be received and displayed on the user interface 170 as well as an average AMS. The multiplier for the base Hypnic Jerk trigger may also be displayed and adjusted through the user interface 170 for the smartphone application 180. In one embodiment, when the user's AMS is higher than the average AMS, then a lower multiplier such as 0.8 may be applied to obtain the user's Hypnic Jerk trigger. Conversely, when the user's AMS is lower than the average AMS, then a higher multiplier such as 1.2 may be applied to obtain the user's Hypnic Jerk trigger. The personalization of the multiplier may be adjusted through using the user interface 170 of the smartphone application 180 and the new personalized Hypnic Jerk trigger may then be transmitted to the alarm system chip 110 through the Bluetooth enabled connection 134 and stored in the memory 136. By personalizing the Hypnic Jerk trigger using the AMS, the user's specific Hypnic Jerk trigger may be adapted to each individual's unique movements.

A Power Nap is generally 10-20 minutes in length during which a sleeper transitions from the Wake stage to NREM 1 (Light Sleep 1), and sometimes to NREM 2 (the second stage of light sleep). This leads to getting the most benefit from a sleep cycle without any grogginess associated with longer sleep duration or waking during Deep Sleep (NREM 3) or REM Sleep. If an individual sleeps longer than 20 minutes, there is a risk of entering deeper sleep and waking up groggy.

Figure 13:
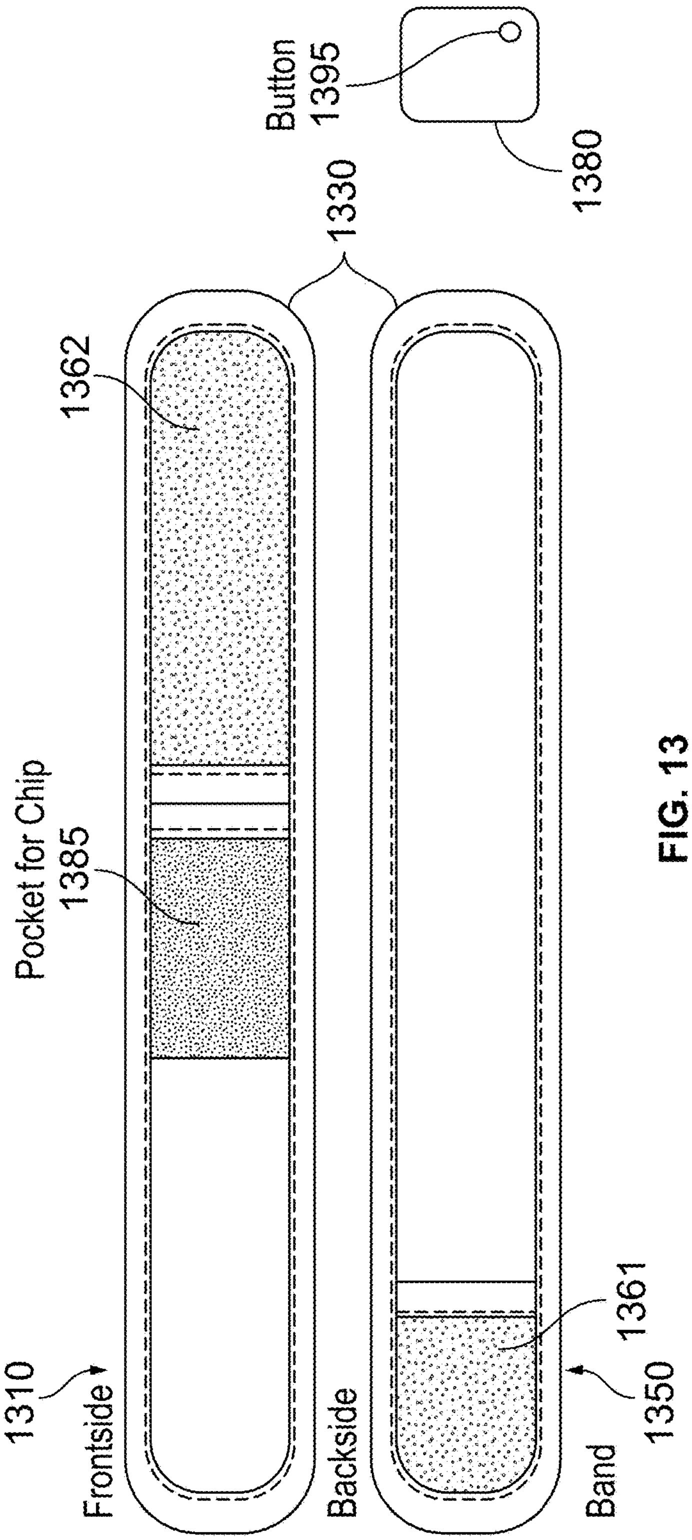
FIG. 13 illustrates an embodiment of the physical appearance of the front view and back view of the band and of the alarm system chip of the present alarm system.

FIG. 13 illustrates an embodiment of the physical appearance of the front view 1310 and back view 1320 of the band and of the alarm system chip 1380 of the present alarm system. As shown in FIG. 13, the alarm system chip 1380 includes the button 1395 which serves as the mechanical switch 195.

The front view 1310 of the band includes a pocket 1385 sized to receive and retain the alarm system chip 1380 when the band is secured around the wrist of a user. The front view 1310 also includes loop area 1362 which is comprised of the "loop" portion of hook-and-loop fastener.

The back view 1350 of the band includes a hook area 1361 which is comprised of the "hook" portion of hook-and-loop fastener. The band also includes a rounded perimeter 1330 comprised of a soft material so as to not disturb a user during sleep. The band may be placed around the wrist of a user and the hook area 1361 may be engaged with the loop area 1362 to secure the band around the wrist of a user.

In one embodiment, the present alarm system 100 may be implemented without the user of the user interface 170 and smartphone application 180 by using the mechanical switch 195 such as a button, as well as the lighting system 160. In one embodiment, the lighting system 160 includes six individual LED lights. To set the alarm, the user may press and hold the button mechanical switch 195 for three second to enter an alarm-set mode. The user may then press then press the button once to switch between the amount of sleep cycles needed with each button press. The number of sleep cycles selected may be displayed by lighting individual ones of the LED lights.

For example, the 6 LED lights in the lighting system 160 may correspond to 6 sleep cycles of approximately 90 minutes each or 9 hours total. Similarly, if 4 sleep cycles have been chosen by button press, then 4 LEDs are illuminated and the alarm system timer may be set for 6 hours from the present time.

The alarm system timer starts counting down once the user long holds the button for 3 seconds. At the initiation of the countdown, the processing system 130 may briefly initiate the vibrating motor of the alarm system to indicate initiation and may also activate a blue LED that is positioned as part of the lighting system. Conversely, if no alarm was set or an alarm time of zero cycles was selected, then after the 3 second hold, the alarm system chip 110 auto sleeps after 60 seconds.

When the user has selected 4 sleep cycles, the processing system 130 automatically establishes a wakeup window (with a default of 45 min) centered around the 6 hour mark making the wake-up window or light sleep detection period start from 5 h 37.5 minutes extending past the 6 hour timer to 6 h 22.5 minutes. In the case of 5 sleep cycles, the wake-up window would be from 7 h 7.5 minutes to 7 h 52.5 minutes of the time the alarm was set.

In one embodiment, the power nap operation may be activated using the mechanical switch 195 by 4 quick presses. Once the command to initiate the power nap is received by the processing unit 130, the processing unit may activate the 6 LEDs of the lighting system 160 to turn green. If the user then holds the button of the mechanical switch 195 for three seconds, the processing unit 130 will initiate the power nap timer for a predetermined nap length of 15 minutes. The processing unit 130 may then briefly initiate the vibrating motor of the alarm system to indicate initiation and may also activate a green LED that is positioned as part of the lighting system. Further, the user interface 170 as part of the smartphone application 180, may be used to adjust defaults, such as the nap length, and communicate the user's selection to the alarm system chip 110 for storage in the memory 136.

In one embodiment, the present system may employ a quick-set mode. In quick-set mode, the user has previously used the user interface 170 and smartphone application 180 to download predetermined settings for the alarm system 110 that are stored in the memory 136. Once the settings have been stored in the memory 136, the user may activate the mechanical switch 195 by holding down a button for 5 seconds. This is received by the processing system 130 which retrieves the predetermined settings from the memory 136 and implements them.

For example, the predetermined settings may include a saved sleep cycle amount and a custom wake-up window. Use of the quick-set mode allows the user to set an alarm in 5 seconds to their usual or preferred alarm settings and also allows a user to activate the alarm system without using the smartphone. Additionally, use of the quick-set mode minimizes the amount of time needed to spend looking at a user interface and promotes a more consistent sleep-length.

In one embodiment of the current alarm system, an alarm may be shut off by using a double press of the button mechanical switch 195 or by using the user interface 170 of the smartphone application 180.

In one embodiment, a single press of the button mechanical switch 195 instructs the processing system 130 to display whether an alarm has been set. In one embodiment, when an alarm has been set, the processing system 130 may activate the lighting system 160 to display a green LED. Conversely, if no alarm has been set, the processing system does not activate the lighting system 160.

In one embodiment, a single press of the mechanical button switch 195 during any wake-up window or light sleep detection period initiates a smart snooze operation as discussed above.

Thus, in one embodiment, the present alarm system chip 110 may be used on daily basis as a standalone device without having to use a smartphone application on a daily basis because the user's preferred settings have already been previously downloaded to the processing system 130 and stored in memory 136 . . . . Further, the present alarm system chip 110 may be equipped with preset defaults for all values discussed herein stored in the memory 136 so that the alarm system chip 110 may be immediately used without a user having to configure defaults using the smartphone application 180.

Additionally, the user of the present alarm system chip 110 without having to employ the user interface 170 of the smartphone application 180 on a daily basis may be desirable because it avoids a user being subject to the light and distraction of a smartphone screen just prior to attempting to initiate sleep.

In one embodiment of the band of FIG. 13, the band may be composed of five fabrics, a binding (self-fabric), a self knit (block fuse), a contrast mesh, a loop fastener, and a hook fastener. In one embodiment, band may be formed by first cutting out the band shape from block fuse material. Second, the self binding may be secured to the edge of the hook, loop, and pocket using an SN lockstitch double fold. Third, SN lockstitch may be employed to clean finish the pocket to the wristband. Fourth, the hook and loop finished edge may be stitched to the edge of the wristband. Fifth, the pocket, hook, and loop may be basted at the edge of the band to ensure the alignment is correct and does not shift. Sixth, the front and back of the wristband may be placed together with fabric side out. SN lockstitch may be employed to finish the double fold self binding to the edge of the wristband. The binding seam overlap may be kept consistent with a placement at the opposite end of the embroidery and the same side.

Figure 14:
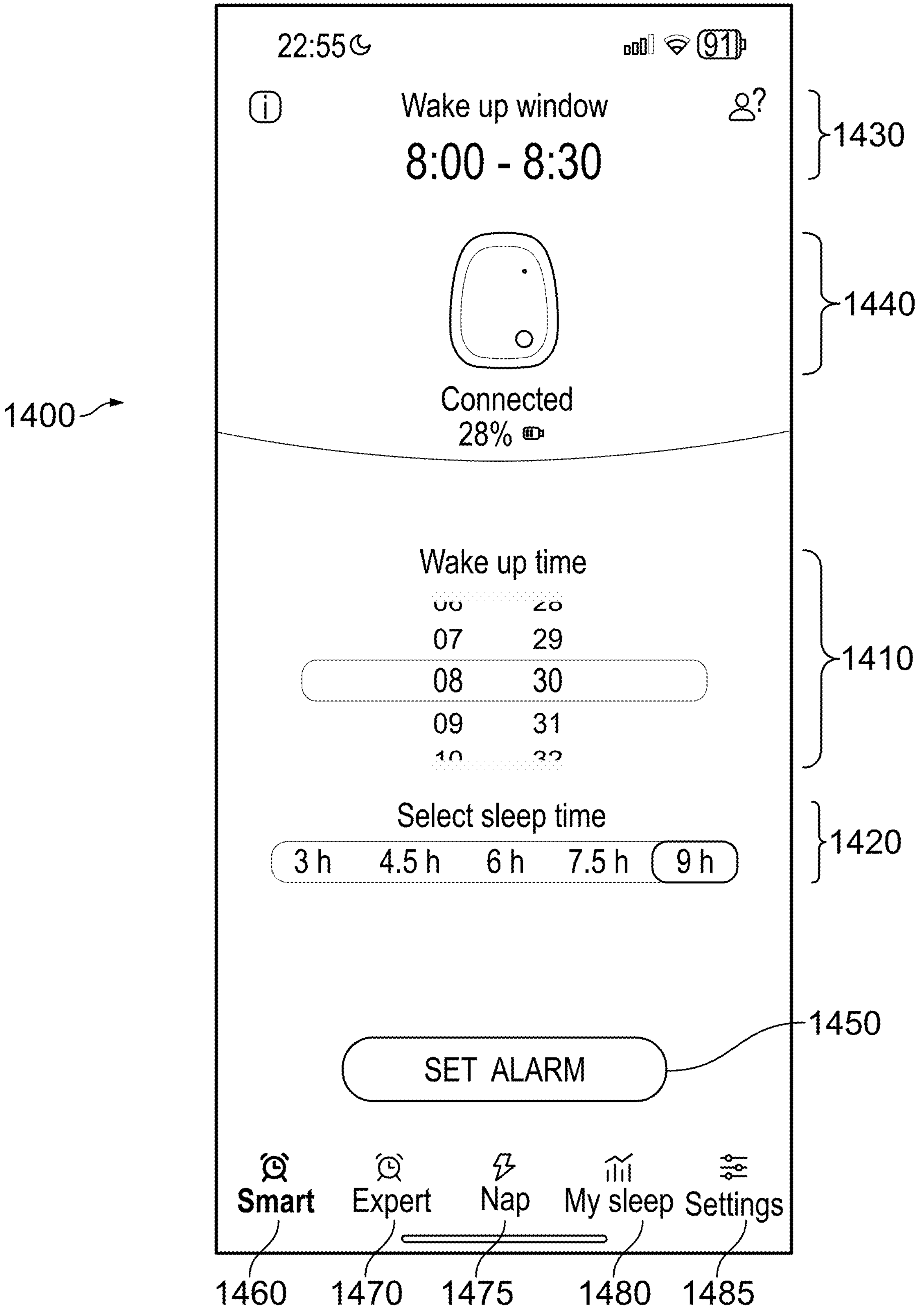
FIG. 14 illustrates an embodiment of a smart alarm setting interface according to an embodiment of the present invention.

FIG. 14 illustrates an embodiment of a smart alarm setting interface 1400 according to an embodiment of the present invention. The smart alarm setting interface 1400 may be displayed as the user interface 170 of the smartphone application 180 and may allow the user to make selections with regard to their sleep program that may then be transmitted to the processing unit 130 of the alarm system chip 110 and stored in the memory 136.

The smart alarm setting interface 1400 includes a wake-time selection scroll wheel 1410 that allows a user to scroll through potential wakeup times for selection.

Similarly, the smart alarm setting interface 1400 includes a sleep-time selection menu 1420 that allows the user to select one of five entries for the length of their sleep program, including 3, 4.5, 6, 7.5 or 9 hours. If the user selects one of the entries in the sleep-time selection menu 1420, the scroll wheel 1410 is automatically adjusted to display the wake-up time. The wake-up time is determined by retrieving the current time from the smartphone's internal clock and then adding the entry selected by the user from the sleep-time selection menu. Reciprocally, if the user adjusts the scroll wheel 1401, when the time displayed on the scroll wheel 1410 matches an entry in the sleep-time selection menu 1420 then that entry is highlighted.

The wakeup window 1430 is determined by subtracting the begin-analysis time offset from the sleep time received through the sleep-time selection menu 1420 or wakeup time received from the wake-time selection scroll wheel 1410. When the smartphone application is in smart mode 1460 as shown in FIG. 14, the application automatically applies 30 minutes as the begin-analysis time offset.

Alarm system status display 1440 provides a graphical representation of the alarm system chip as well as an indication of whether the Bluetooth connection between the smartphone application 180 and alarm system chip 110 is connected. Additionally, the current charging level of the alarm system chip is displayed. As shown in FIG. 14, the smartphone application 180 and alarm system chip 110 are currently connected and the alarm system chip's charging level is 28%.

Once the smart alarm setting interface 1400 has received either the user's desired wakeup time or the user's desired sleep time, these are passed to the smartphone application 180 which applies the predetermined, stored begin-analysis offset and displays wake-up window. The user may then set the alarm using the alarm set button 1450 at which point the smartphone application transmits the wakeup time and begin-analysis time to the alarm system chip 110 for use. If the user's threshold triggers have not already been transmitted to the alarm system chip, then they are also transmitted at this time.

At the bottom of the smart alarm setting interface 1400 is a smart mode selection button 1460, an expert mode selection button 1470, a nap mode selection button 1475, a My sleep selection button 1480, and a settings selection button 1485. Selection or activation of the smart mode selection button 1460, expert mode selection button 1470, and nap mode selection button 1475 allows a user to cause the smartphone application to display those respective user interfaces. Selection of the My sleep selection button 1480 displays information about the user's previous sleep experiences including AWS, average time of sleep and other user-specific information mentioned above. Selection of the settings button 1485 causes the smartphone application to display setup information for the current user, including for example, the user's AMS, threshold trigger, or any other information mentioned above.

Figure 15:
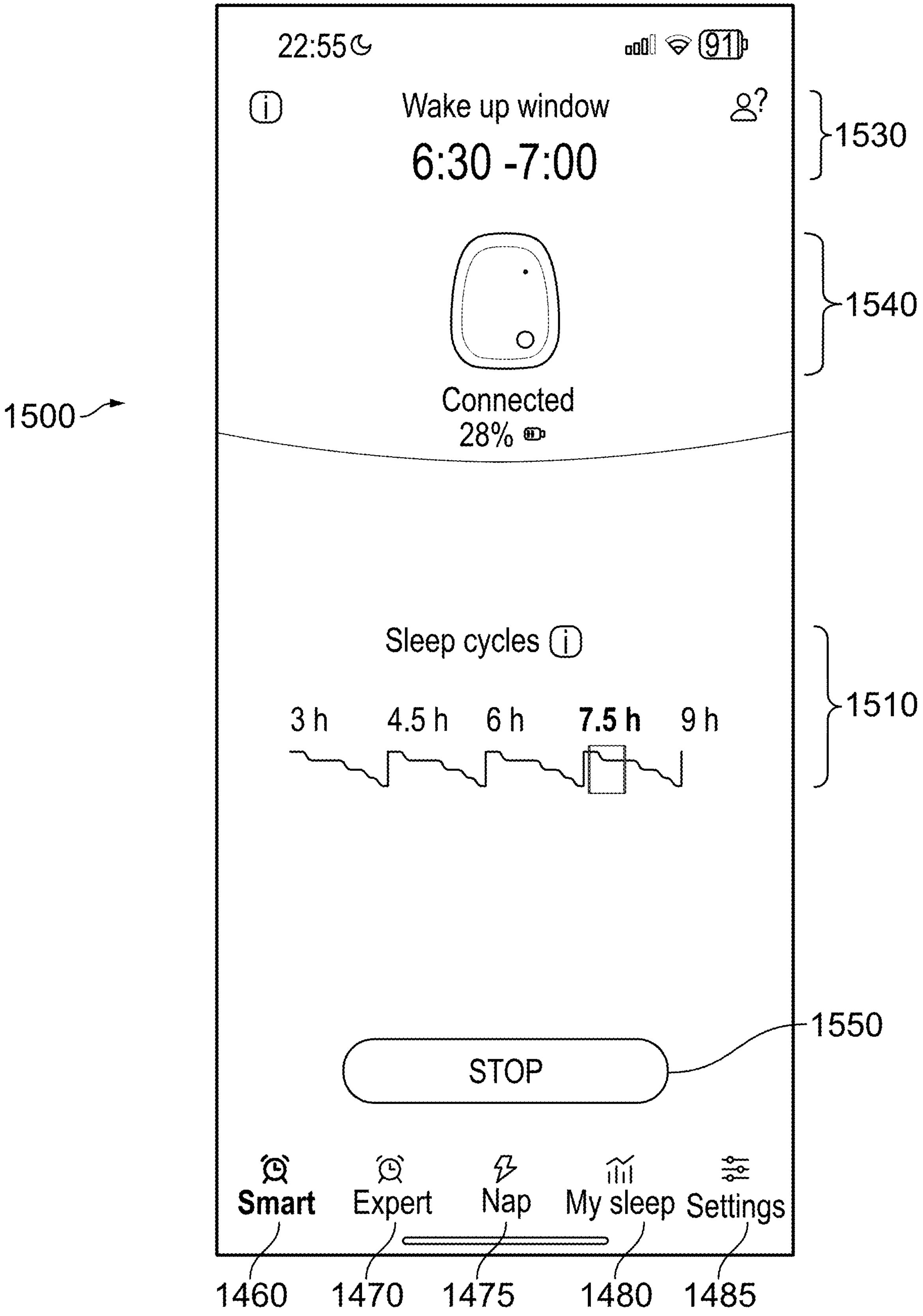
FIG. 15 illustrates an alarm-engaged interface according to an embodiment of the present invention.

FIG. 15 illustrates an alarm-engaged interface 1500 according to an embodiment of the present invention. FIG. 15 includes a wake-up window 1530 displaying the begin-analysis time and latest wakeup times selected by the user. FIG. 15 also includes the alarm system status display 1540 similar to the alarm system status display 1440 in FIG. 14.

Stop button 1550 may be activated by the user to stop the current alarm program, to shut off an alarm once an alarm has been initiated, or may be used to activate the smart snooze operation. For example, one tap may enter smart snooze and two taps may shut off the current alarm Sleep cycle status display 1510 may illustrate the user's current sleep state vertically on the y-axis with lighter sleep states being higher and lower sleep states such as REM sleep being lower. Additionally, the sleep cycle status display 1510 may display the user's current sleep cycle and approximately how long the user has been asleep.

At the bottom of the alarm-engaged interface 1500 are the smart mode selection button 1460, expert mode selection button 1470, nap selection button 1475, My sleep selection button 1480, and settings selection button 1485.

Figure 16:
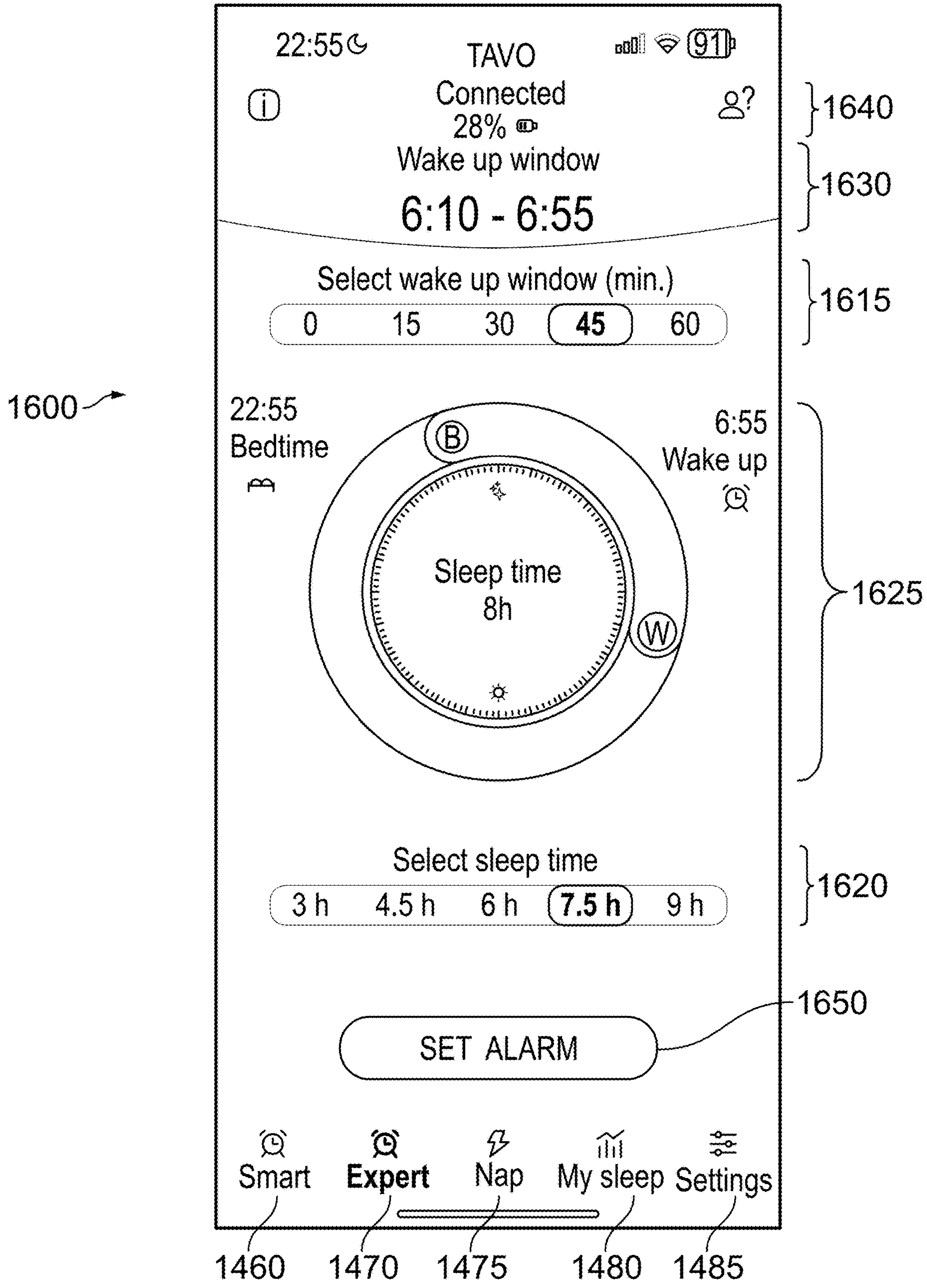
FIG. 16 illustrates an embodiment of an expert alarm setting interface according to an embodiment of the present invention.

FIG. 16 illustrates an embodiment of an expert alarm setting interface 1600 according to an embodiment of the present invention. One major difference from the interface of FIG. 14 is that the expert alarm setting interface 1600 allows a user to select the length of their desired begin-analysis time offset using the wakeup time offset selection window 1615. In the wakeup time offset selection window 1615, the user may select offsets of 1, 15, 30, 45, or 60 minutes to be used. In operation, similarly to the 30-minute offset, offsets of different times are also divided into 15 intervals representing $\frac{1}{15}^{th}$ of the offset time. The detection of trigger events and interval-by-interval analysis may then proceed similarly as discussed above with regard to the 30-minute offset. Additionally, the number of intervals may be adjusted to a number other than 15, such as 10, 20, or 30.

FIG. 16 includes a wake-up window 1630 displaying the begin-analysis time and latest wakeup times selected by the user. FIG. 16 also includes the alarm system status display 1640 similar to the alarm system status display 1440 in FIG. 14, but without the graphical representation of the alarm system chip 110. FIG. 16 also includes the sleep-time selection menu 1620 similar to the sleep-time selection menu 1420 of FIG. 14 as well as the alarm set button 1650 similar to the alarm set button 1450.

Figure 17:
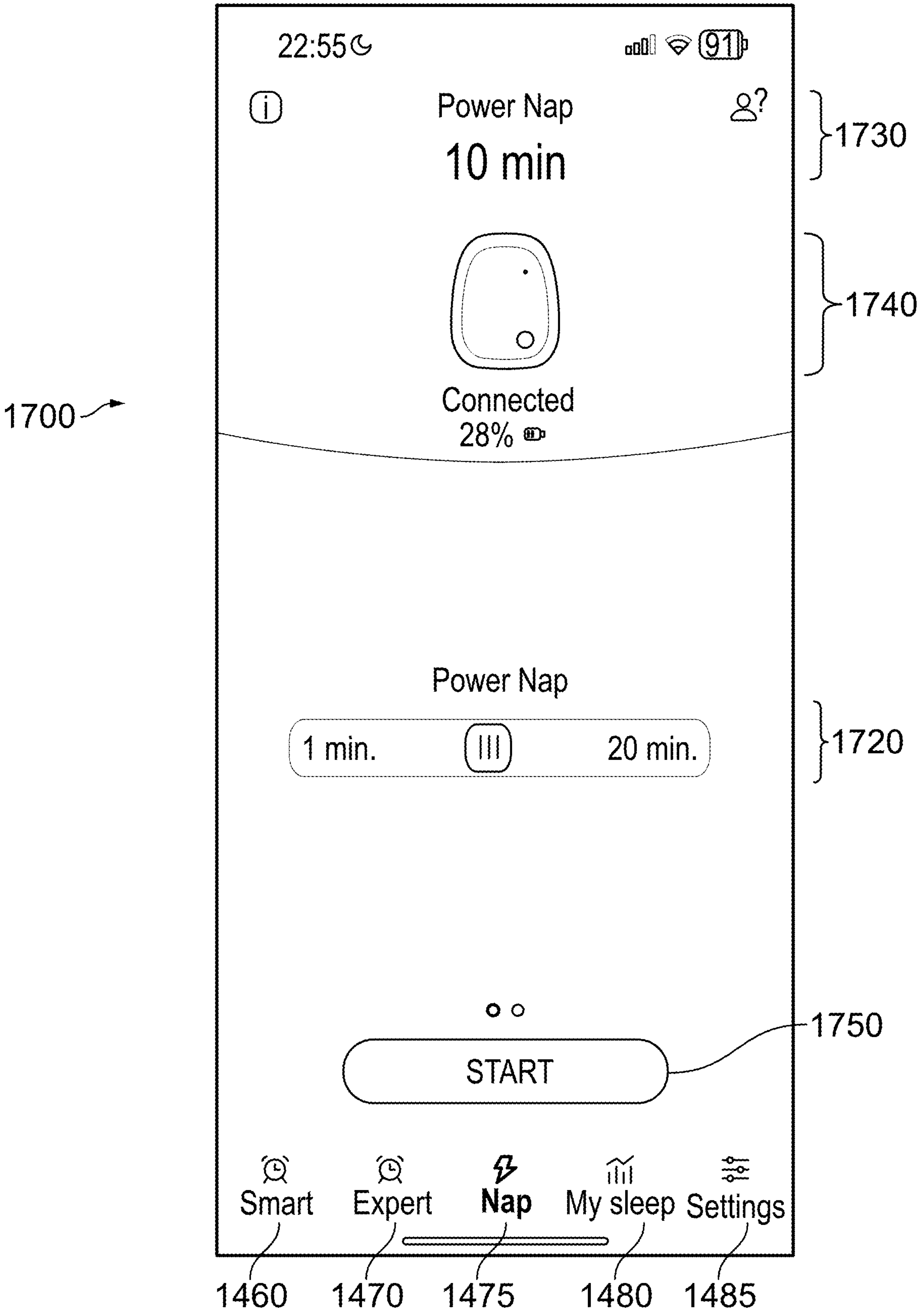
FIG. 17 illustrates an embodiment of a power nap setting interface according to an embodiment of the present invention.

FIG. 17 illustrates an embodiment of a power nap setting interface 1700 according to an embodiment of the present invention. FIG. 17 shows a nap length display 1730 displaying the nap length selected by the user. Also shown is the alarm system status display 1740 similar to the alarm system status display 1440 of FIG. 14.

FIG. 17 also shows a nap time selection slidebar 1720. The nap time selection slidebar 1720 allows a user to slide between times of 1 minute to 20 minutes to select a desired nap time. The nap time selected by the user is the displayed in the nap length display 1730. Additionally, the map start button 1750 begins the power nap at which point the smartphone application transmits the nap time to the alarm system chip 110 for use. If the user's threshold triggers have not already been transmitted to the alarm system chip, then they are also transmitted at this time.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

The invention claimed is:

1. An alarm system to awaken a user, said system including:
- a processing system including a clock providing a current time;
- a memory storing:
  - a latest wakeup time entered by said user;
  - a begin-analysis time;
  - a begin-analysis time offset representing an amount of time prior to the latest wakeup time to determine said begin-analysis time;
  - an interval number; and
  - a user movement threshold trigger;
- a sensor system receiving accelerometer data from an accelerometer affixed to said user; and
- an alarm system,
- wherein, once said processing system determines that the current time has reached said begin-analysis time using said clock, said processing system divides said amount of time indicated by said begin-analysis time offset by said interval number to determine a plurality of intervals and stores in said memory an entry for each interval of said plurality of intervals including:

a sequential numeric indicator of said interval;

a start time of said interval; and a number of times indicative of said accelerometer data exceeding a user movement threshold trigger has been detected for said interval, wherein said processing system compares said current time received from said clock to said start time of said interval to determine a current interval, wherein said processing system receives said accelerometer data and when said accelerometer data indicates movement greater than said user movement threshold trigger, said processing system increments said number of times and stores in memory said number of times for said current interval, wherein, when said number of times for said current interval equals three, said processing system sets an activated status indicator for said current interval to an activated status and said processing system determines a previous interval by decrementing the sequential numeric indicator of said current interval to retrieve an activated status indicator for said previous interval, wherein when said activated status indicator for said previous interval is an activated status indicative of a number of times said accelerometer data exceeding said user movement threshold trigger has been detected for said previous interval also equals or exceeds three, said processing system initiates said alarm system to awaken said user.

2. The system of claim 1 wherein said processing system receives said latest wakeup time and determines said begin-analysis time by subtracting said begin-analysis time offset from said latest wakeup time.

3. The system of claim 1 wherein said interval number is 15.

4. The system of claim 1 wherein said begin-analysis offset time is 30 minutes.

5. The system of claim 1 wherein said intervals are 2 minutes in length.

6. The system of claim 1 wherein said user movement threshold trigger is 1.2 $m/s^2$.

7. The system of claim 1 wherein said user movement threshold trigger is adjustable by said user.

8. The system of claim 1 wherein one or more of said begin-analysis time, said begin-analysis time offset, said interval number; and said user movement threshold trigger, are received by said processing system from a smartphone application.

9. The system of claim 8 wherein said smartphone application communicates with said processing system using Bluetooth communication protocol.

10. A method for activating an alarm system to awaken a user, said method including:

storing in a memory:

a latest wakeup time entered by said user;

a begin-analysis time;

a begin-analysis time offset representing an amount of time prior to the latest wakeup time to determine said being-analysis time;

an interval number; and a user movement threshold trigger;

receiving accelerometer data from an accelerometer affixed to said user at a processing system including a clock providing a current time and in communication with said memory;

wherein, once said processing system determines that the current time has reached said begin-analysis time using said clock, said processing system divides said amount of time indicated by said begin-analysis time offset by said interval number to determine a plurality of intervals and stores in said memory an entry for each interval of said plurality of intervals number including:

a sequential numeric indicator of said interval;

a start time of said interval; and a number of times indicative of said accelerometer data exceeding a user movement threshold trigger has been detected for said interval, wherein said processing system compares said current time received from said clock to said start time of said interval to determine a current interval, wherein said processing system receives said accelerometer data and when said accelerometer data indicates movement greater than said user movement threshold trigger, said processing system increments said number of times and stores in memory said number of times for said current interval, wherein, when said number of times for said current interval equals three, said processing system sets an activated status indicator for said current interval to an activated status and said processing system determines a previous interval by decrementing the sequential numeric indicator of said current interval to retrieve an activated status indicator for said previous interval, activating an alarm system to awaken said user in response to said processing system determines said activated status indicator for said previous interval being an activated status indicative of a number of times said accelerometer data exceeding said user movement threshold trigger has been detected for said previous interval also equals or exceeds three.

11. The method of claim 10 wherein said processing system receives said latest wakeup time and determines said begin-analysis time by subtracting said begin-analysis time offset from said latest wakeup time.

12. The method of claim 10 wherein said interval number is 15.

13. The method of claim 10 wherein said begin-analysis offset time is 30 minutes.

14. The method of claim 10 wherein said intervals are 2 minutes in length.

15. The method of claim 10 wherein said user movement threshold trigger is 1.2 $m/s^2$.

16. The method of claim 10 wherein said user movement threshold trigger is adjustable by said user.

17. The method of claim 10 wherein one or more of said begin-analysis time, said begin-analysis time offset, said interval number; and said user movement threshold trigger, are received by said processing system from a smartphone application.

18. The method of claim 17 wherein said smartphone application communicates with said processing system using Bluetooth communication protocol.

* * * * *